United States Patent
Park et al.

(10) Patent No.: US 10,816,412 B2
(45) Date of Patent: Oct. 27, 2020

(54) THERMOMETER AND BODY TEMPERATURE MEASURING APPARATUS INCLUDING THE SAME

(71) Applicant: LG ELECTRONICS INC., Seoul (KR)

(72) Inventors: Hyungwoo Park, Seoul (KR); Hyunkyung Yoo, Seoul (KR); Sungwon Kim, Seoul (KR); Jeongsoo Park, Seoul (KR); Taehoon Yoo, Seoul (KR); Sehyun Han, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 214 days.

(21) Appl. No.: 15/926,439

(22) Filed: Mar. 20, 2018

(65) Prior Publication Data

US 2018/0274990 A1  Sep. 27, 2018

Related U.S. Application Data

(60) Provisional application No. 62/474,094, filed on Mar. 21, 2017.

(30) Foreign Application Priority Data

Apr. 28, 2017  (KR) .......................... 10-2017-0055572

(51) Int. Cl.
*G01J 5/00* (2006.01)
*G01K 13/00* (2006.01)
(Continued)

(52) U.S. Cl.
CPC .......... *G01K 13/004* (2013.01); *A61B 5/0008* (2013.01); *A61B 5/0022* (2013.01);
(Continued)

(58) Field of Classification Search
CPC ...... G01J 5/025; G01J 5/10; G01J 5/04; G01J 5/32; G01J 5/00; A61B 5/02433;
(Continued)

(56) References Cited

U.S. PATENT DOCUMENTS 4,634,294 A * 1/1987 Christol .................... G01J 5/02
                                                    340/584
6,402,371 B2 * 6/2002 Pompei ................. G01J 5/0022
                                                    250/338.1

(Continued)

FOREIGN PATENT DOCUMENTS

| JP | 2010-82010 A | 4/2010 |
| JP | 2010-131209 A | 6/2010 |
| JP | 2017-3538 A | 1/2017 |
| KR | 10-2007-0042644 A | 4/2007 |
| WO | WO 2016/083807 A1 | 6/2016 |

*Primary Examiner* — Gail Kaplan Verbitsky
(74) *Attorney, Agent, or Firm* — Birch, Stewart, Kolasch & Birch, LLP

(57) ABSTRACT

A thermometer is provided that includes a main body having a first body including first and second regions and a second body mounted on the first body, the main body extending in a first direction; a rubber cap surrounding the second region and formed to be inserted into the ear; a temperature sensor disposed in the second region and having a specific temperature sensing range with respect to the first direction; and first and second circuit boards electrically connected to the temperature sensor and disposed in the second region in a second direction intersecting the first direction.

14 Claims, 32 Drawing Sheets

(51) Int. Cl.
  *G01K 1/02* (2006.01)
  *G01V 3/08* (2006.01)
  *A61B 5/00* (2006.01)
  *G01J 5/02* (2006.01)
  *G01V 8/00* (2006.01)
  *A61B 5/01* (2006.01)

(52) U.S. Cl.
  CPC .............. *A61B 5/01* (2013.01); *A61B 5/6817* (2013.01); *G01J 5/025* (2013.01); *G01J 5/0265* (2013.01); *G01K 1/024* (2013.01); *G01V 3/08* (2013.01); *G01V 8/00* (2013.01)

(58) Field of Classification Search
  CPC .......... A61B 2562/0271; A61B 5/0086; A61B 5/14552; G01K 13/004; G01K 13/002; G01K 1/02
  USPC ................ 374/121, 158, 163, 170; 702/135; 600/474, 549, 184
  See application file for complete search history.

(56) References Cited

U.S. PATENT DOCUMENTS

| | | | |
|---|---|---|---|
| 6,513,970 B1* | 2/2003 | Tabata | G01J 5/0003 374/102 |
| 7,338,206 B2* | 3/2008 | Yu | G01J 5/02 374/121 |
| 9,055,924 B2* | 6/2015 | Roth | A61B 5/6887 |
| 9,739,665 B2* | 8/2017 | Hagl | A61B 5/14546 |
| 2001/0014112 A1* | 8/2001 | Yamaka | G01J 5/02 374/158 |
| 2005/0083991 A1* | 4/2005 | Wong | G01J 5/02 374/131 |
| 2007/0055171 A1* | 3/2007 | Fraden | G01K 1/165 600/549 |
| 2011/0228811 A1* | 9/2011 | Fraden | G01J 5/061 374/130 |
| 2012/0114160 A1 | 5/2012 | Lin | |

* cited by examiner

THERMOMETER AND BODY TEMPERATURE MEASURING APPARATUS INCLUDING THE SAME

CROSS-REFERENCE TO RELATED APPLICATION

Pursuant to 35 U.S.C. § 119, this application claims the benefit of earlier filing date and right of priority to U.S. Provisional Application No. 62/474,094, filed on Mar. 21, 2017, and Korean Application No. 10-2017-0055572, filed on Apr. 28, 2017, the entire contents of which are hereby incorporated by reference.

BACKGROUND OF THE INVENTION

1. Field of the Invention

The present invention relates to a thermometer configured to be inserted into an ear for sensing a body temperature.

2. Background of the Invention

Body temperature measuring apparatuses include a temperature sensor and are inserted into a mouth or an ear to measure a temperature. However, these apparatuses acquire information on a body temperature in a state that they are inserted into a part of a body for a specific time while they are held in the hand. That is, these apparatuses are not body-mounted apparatuses.

A body temperature starts to rise as a person wakes up in the morning, peaks in the afternoon and then falls at night. A basal body temperature refers to a low body temperature in the most stable state, and useful information on the menstruation/ovulation cycle of women may be obtained by recording daily basal body temperature. To measure such a basal body temperature, it is necessary for a person to take at least 3-4 hours of sleep and then measure a body temperature in the most stable state. Since most thermometers need to be manipulated personally, it is not possible to measure a body temperature during sleep, and therefore, it is necessary to minimize movement in a wake-up state and measure a body temperature. However, a lot of movement is already made at the stage of bringing the thermometer into contact with the body and a change in a direction or position in which the thermometer is inserted may cause plenty or errors in the measurement of the basal body temperature.

A recently developed wearable-type thermometer has a problem in that when a user sleeps with the thermometer worn on the ear, the bulky thermometer interferences with sleeping or makes the user feel stuffy due to the clogged ear and since it is inserted into the inside of the auricle, wearability is not good.

SUMMARY OF THE INVENTION

It is an object of the present invention to solve the above and other problems and to provide a thermometer which has improved wearability, while minimized in volume.

According to an aspect of the present invention, to achieve the above and other objects, a thermometer according to an embodiment of the present invention comprises a main body having a first body including first and second regions and a second body mounted on the first body, the main body extending in a first direction; a rubber cap surrounding the second region and formed to be inserted into the ear; a temperature sensor disposed in the second region and having a specific temperature sensing range with respect to the first direction; and first and second circuit boards electrically connected to the temperature sensor and disposed in the second region in a second direction intersecting the first direction, wherein the first body and the rubber cap include first and second holes for exposing the temperature sensor, and wherein the first body has one end cut along the second direction, and the second body is mounted on the one end of the first body.

In one embodiment, the inner surface of the second region forming the first hole may be an oblique surface, the inner surface of the rubber cap forming the second hole may be an oblique surface, and the first and second oblique surfaces are formed such that the first and second holes become larger as the distance from the temperature sensor increases, and the first and second oblique surfaces have a specific angle to include the sensing range. Accordingly, the sensing region of the temperature sensor is not blocked and a temperature of a specific region of the ear formed with the eardrum can be accurately measured.

In one embodiment, the thermometer further comprises a vent hole extending from the end of the second region to a boundary of the first and second regions and being formed by recessing an outer surface of the second region. Air can inflow into the vent hole by a gap between the first and second regions and the rubber cap and accordingly, air and moisture can pass through the vent hole and the accuracy of the sensor can be consistently maintained, thereby improving the comfort.

According to the present invention, a circuit board is disposed in a direction oblique to the direction in which the temperature sensor is disposed and therefore, it is possible to minimize the volume of the thermometer while securing the width of the circuit board Accordingly, it is possible to implement a thermometer in a shape elongated in one direction to thereby reduce any inconvenience while sleeping with the thermometer in the ear by minimizing a contact area to the outside of the ear such as the auricle when worn.

A vent hole is formed in one region of the first body wrapped with the rubber cap to thereby minimize a boredom and the vent hole is formed on the outside of the main body thereby preventing foreign matters from entering the internal electronic components. Further, moisture can be prevented from getting inside the ear by circulating air through the vent hole.

DETAILED DESCRIPTION OF THE INVENTION

Figure 1A:
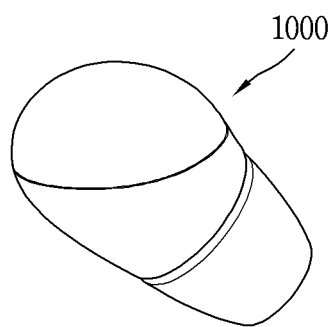
FIG. 1A is a view showing a thermometer according to an embodiment of the present invention, viewed from one direction.

Hereinafter, preferred embodiments of the present invention will be described in detail with reference to the accompanying drawings, wherein like reference numerals refer to the same or like elements throughout the drawings. The terms "module" and "unit" as used in the following description are given or mixed in consideration of ease of specification, and do not have their own distinct meaning or role. Further, in the following description of the embodiments of the present invention, a detailed description regarding related arts will be omitted when it is considered that the gist of the embodiments disclosed herein may be obscured. It should be understood that the attached drawings are intended only for easy understanding of the embodiments disclosed in the present invention, not restriction of the technical idea disclosed in the specification and thus they are intended to cover all modifications, equivalents, and alternatives falling within the spirit and scope of the invention.

Figure 1B:
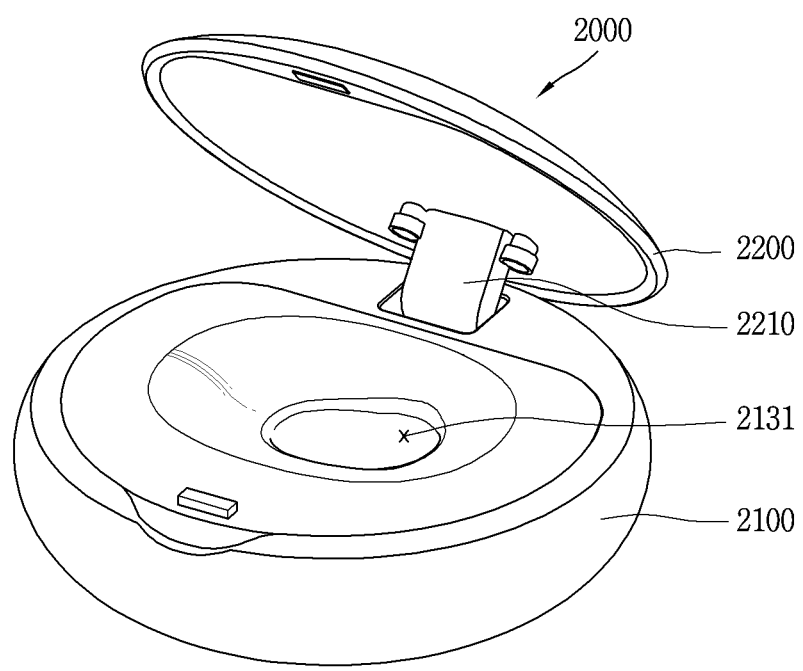
FIG. 1B is a view of a receiving device for receiving the thermometer of FIG. 1a, viewed from other direction.
Figure 1C:
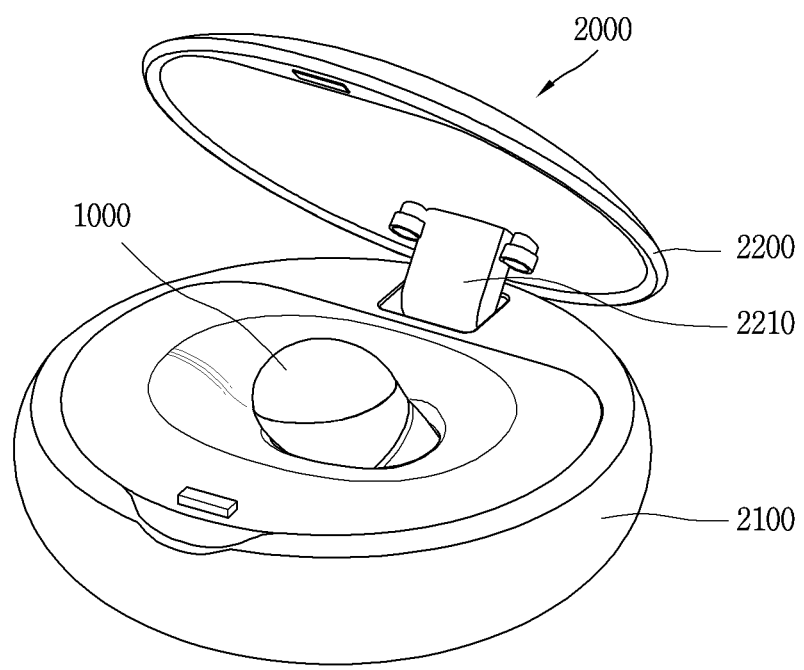
FIG. 1C is a conceptual diagram illustrating a state that a thermometer is received in a receiving device.
Figure 1D:
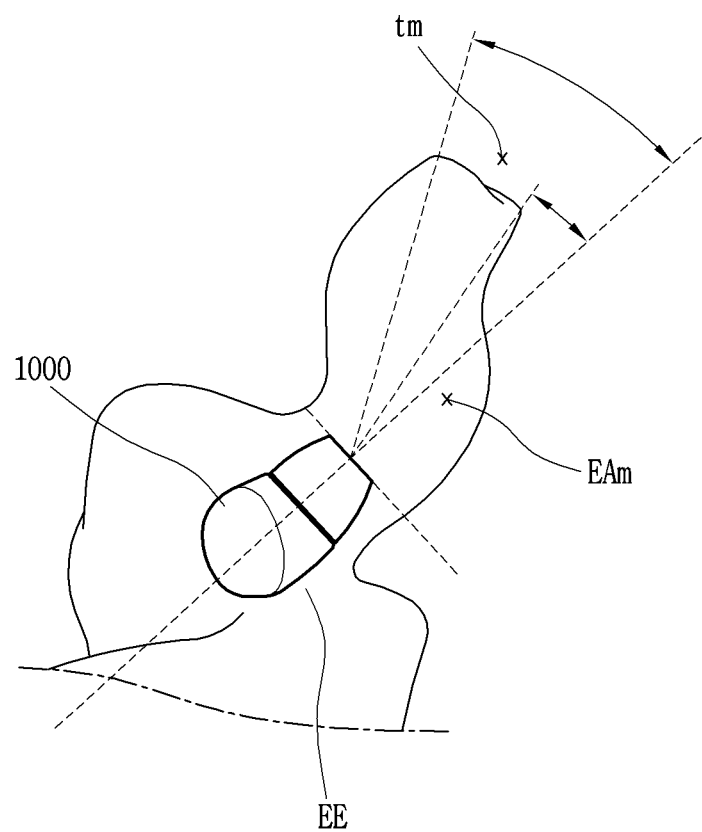
FIG. 1D is a schematic view showing a wearing state of the thermometer.

FIG. 1A is a view showing a thermometer according to an embodiment of the present invention, viewed from one direction. FIG. 1B is a view of a receiving device for receiving the thermometer of FIG. 1A, viewed from other direction. FIG. 1C is a conceptual diagram illustrating a state that a thermometer is received in a receiving device. FIG. 1D is a schematic view showing a wearing state of the thermometer.

Referring to FIGS. 1A to 1D, a thermometer 1000 has a shape that can be inserted into a human ear. The human ear has an eardrum (tm) which is placed at the end of an external ear (EE) through an external ear canal (EAM). The thermometer 1000 according to the present invention is disposed in the external ear canal (EAM). One region of the thermometer 1000 is formed to be inserted into the external ear canal (EAM). A sensor for measuring the body temperature is disposed at one end of the thermometer 1000. When the thermometer 1000 is inserted into the external ear canal (EAM), the sensor is arranged to face the eardrum (tm). Accordingly, the sensor can measure a body temperature emitted from the eardrum (tm).

If the thermometer 1000 is separated from the user's ear, the thermometer 1000 is received in the receiving device 2000. The receiving device 2000 includes a body portion 2100, a lid portion 2200 and a connection portion 2210 connecting the lid portion 2200 to the body portion 2100. The lid portion 2200 is rotatably fixed to the body portion 2100 by the connection portion 2210 so as to open or close the body portion 2100.

The body portion 2100 includes a concave shaped receiving region 2131 in which the thermometer 1000 is received. The thermometer 1000 may perform wireless communications with an external device in a state of being seated in the receiving region 2131 or may be protected when not used. Referring to FIG. 1C, one region of the thermometer 1000 protrudes from the surface of the body portion 2100 in a state of being seated in the receiving region 2131, and the cover portion 2200 is concave-shaped so as to cover it.

Hereinafter, a structure of the thermometer 1000 inserted into the human ear for measuring the body temperature will be described.

Figure 2:
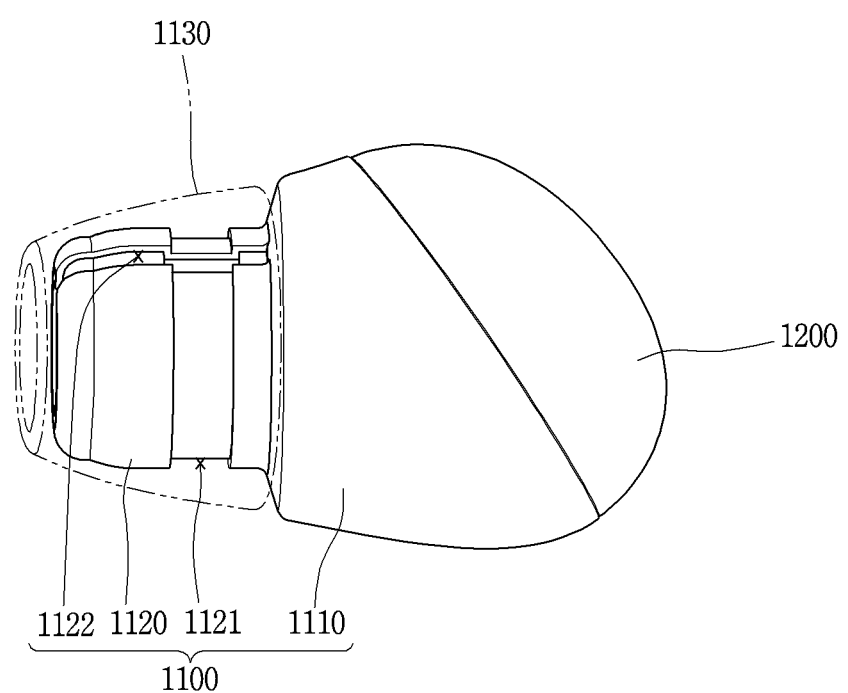
FIG. 2 is a view of the thermometer of FIG. 1A, viewed from another direction.

FIG. 2 is a view of the thermometer of FIG. 1A, viewed from other direction.

Referring to FIG. 2, the thermometer 1000 includes a first body 1100 and a second body 1200. The first and second bodies 1100 and 1200 may be detachably coupled to each other.

The first body 1100 includes a first region 1110 and a second region 1120 protruding from the first region 1110. The outer circumference of the second region 1120 may be formed smaller than the outer circumference of the first region 1110. A rubber cap 1130 made of a rubber material is formed in the second region 1120. The rubber cap 1130 is inserted into the external ear canal of the ear and can be elastically deformed and prevented from being separated from the ear due to a large frictional force on the surface of the rubber cap 1130.

The outer peripheral surface of the rubber cap 1130 may form one surface with the outer peripheral surface of the first region 1110, and the rubber cap 1130 is formed to be separable from the second region 1120.

The second region 1120 includes a fixing groove 1121 for fixing the rubber cap 1130 and a vent hole 1122 for allowing air to move. The fixing groove 1121 is recessed such that one region of the outer circumferential surface of the second region 1120 may have a specific width. Although not specifically illustrated in FIG. 2, the rubber cap 1130 may further include fixing protrusions that protrude from the inner circumferential surface of the rubber cap 1130 and are fitted into the fixing grooves 1121. Accordingly, if the rubber cap 1130 is secured to the second region 1120 and an external force is applied to the second region 1120 and the rubber cap 1130, the fixing protrusion may be elastically deformed and separated from the second region 1120.

Meanwhile, the vent hole 1122 is formed in the extending direction of the second region 1120, and one region of the second region 1120 is formed by being recessed. The vent hole 1122 is formed from the end of the second region 1120 to the boundary region of the first and second regions 1110 and 1120.

One region of the vent hole 1122 is formed deeper than the fixing groove 1121. Therefore, even if the fixing protrusion is inserted into the fixing groove 1121, air can pass through the one region of the vent hole 1122.

A space is formed between the second region 1120 and the rubber cap 1130 by the vent hole 1122. In the state that the second region 1122 having the rubber cap 1130 mounted has been inserted into the ear, one end of the vent hole 1122 is arranged inside of the ear, the other end of the vent hole 1120 is exposed to the outside of the ear. Air can pass through the vent hole 1122 into and out of the ear.

When one end of the vent hole 1122 is at the exposed state by the end of the second region 1120, air can pass through a gap between the first region and the rubber cap 1130 to the vent hole 1122.

Therefore, since the thermometer 1000 is configured to allow air to pass through it even in the state where the thermometer 1000 closes the ear, it is possible to dust the boredom caused by the pressure difference.

Further, since the vent hole of the thermometer 1000 of the present invention is formed on the outer surface of the first body 1110, it is not necessary to penetrate the inside of the first body 1110. Therefore, a problem that foreign substances, etc. enter the inside of the first body through the vent hole can be avoided whereby it is possible to minimize a damage of electronic components (sensor, circuit board, etc.) that are disposed in the inside of the first body 1110.

Moisture can be prevented from being drawn by the vent hole, and a plurality of vent holes can be formed in the first body portion.

Figure 3A:
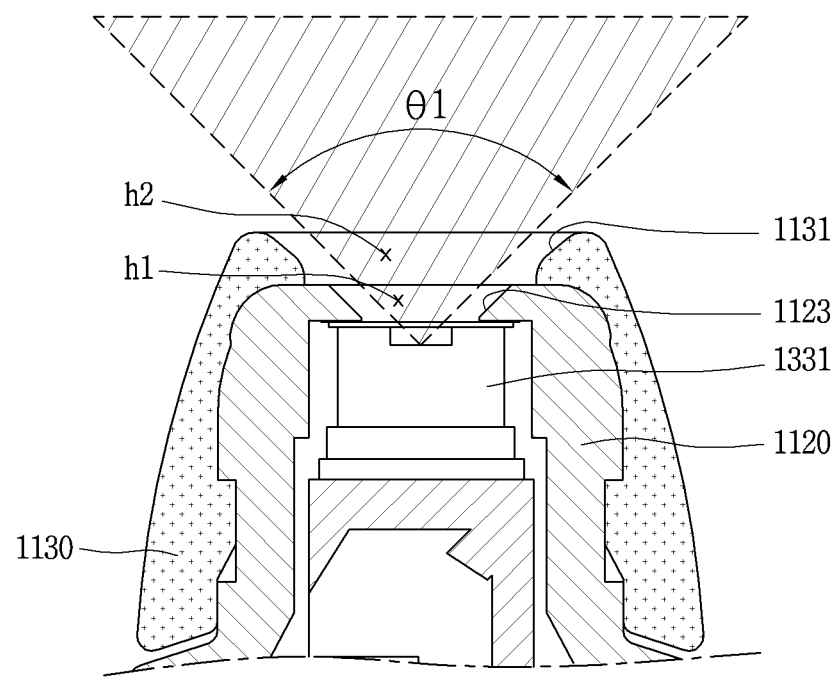
FIGS. 3A and 3B are conceptual diagrams illustrating a second region based on a sensing range of a sensing unit and a structure of a rubber cap.
Figure 3B:
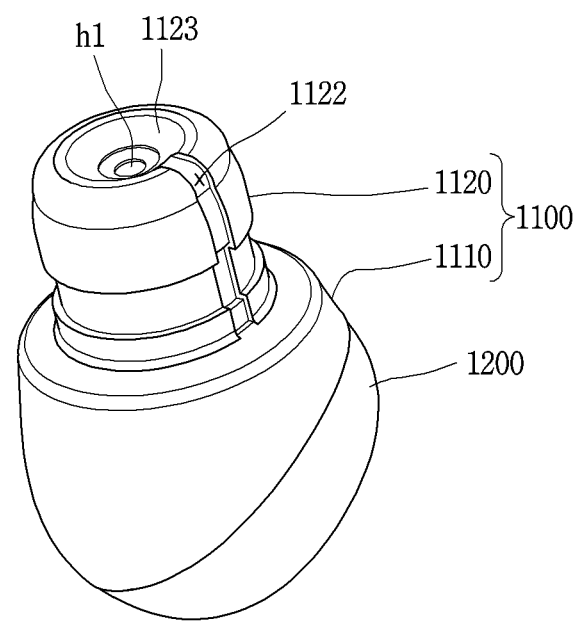

FIGS. 3A and 3B are schematic diagrams illustrating the structure of the second region and the rubber cap based on the sensing range of the sensor unit.

A temperature sensor 1331 is disposed at an end of the first body 1100 to sense a temperature. The temperature sensor 1331 may be implemented as a non-contact type infrared sensor. The infrared sensor receives the infrared energy emitted from the body by an IR sensor and converts it into a measurable electrical signal.

The temperature sensor 1331 has a specific sensing range θ1. For example, the sensing range or Field of View (FOV) θ1 of the temperature sensor 1331 may correspond to about 100 degrees. The temperature sensor 1331 is configured to sense a temperature within a certain angle range with respect to the center.

The ends of the second region 1120 and the rubber cap 1130 surrounding the temperature sensor 1331 include first and second holes h1 and h2, respectively. The first hole h1 is formed at an end of the second region 1120, and the temperature sensor 1331 is exposed. The size of the first hole h1 may be formed smaller than the end of the temperature sensor 1331. The inner surface of the second region 1120 forming the first hole h1 is composed of an oblique surface 1123. The oblique surface 1123 forms a certain angle from the temperature sensor 1331 and is formed in a direction in which the size of the first hole h1 widens as the distance from the temperature sensor 1331 increases. The certain angle is formed to be equal to or greater than an angle corresponding to the sensing range of the temperature sensor 1331. That is, the first hole h1 is formed to include the sensing range of the temperature sensor 1331.

Meanwhile, the rubber cap 1130 includes the second hole h2 corresponding to the first hole h1. The second hole h2 is located farther from the temperature sensor 1331 than the first hole h1 and is formed to be larger than the first hole h1. The first and second holes h1 and h2 communicate with each other and the centers of the first and second holes h1 and h2 may correspond to each other.

The inner surface of the rubber cap 1130 forming the second hole h2 is formed as an oblique surface 1131. The oblique surface also forms a specific angle, and the second hole h2 is formed to be larger as the distance from the temperature sensor 1331 increases. The inclination of the oblique surface 1131 forming the second hole h2 may be substantially equal to the inclination of the oblique surface 1123 forming the first hole h1. Alternatively, the degree of inclination of the oblique surface of the second hole h2 may be larger.

The sensing range of the temperature sensor 1331 is not blocked by the first and second holes h1 and h2. Accordingly, the function of the temperature sensor 1331 can be improved.

Figure 4A:
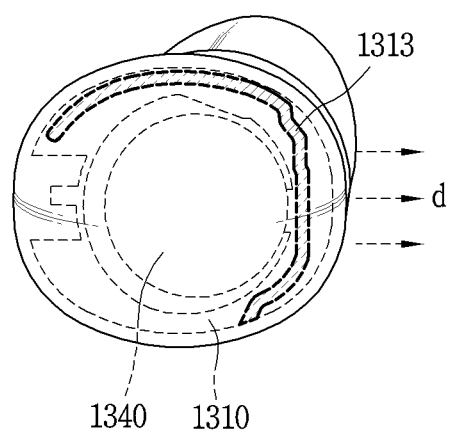
FIG. 4A is a conceptual diagram showing an arrangement of an antenna of a temperature sensor device.
Figure 4B:
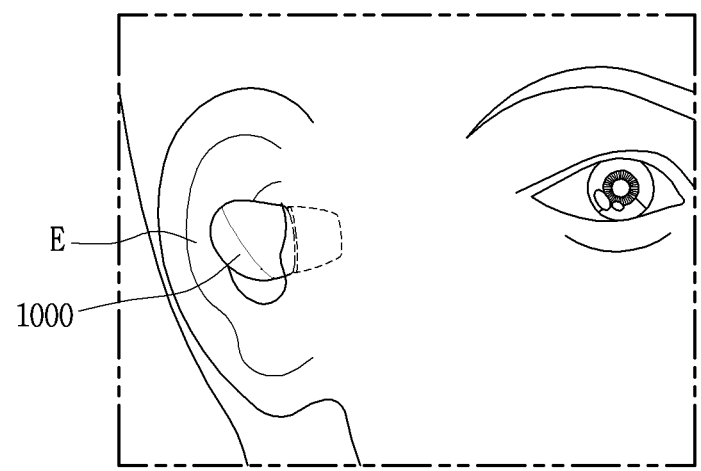
FIG. 4B is a conceptual diagram illustrating a direction of wireless communication in a state of being inserted into an ear.

FIG. 4A is a schematic view showing the arrangement of the antennas of the temperature sensor device, and FIG. 4B is a schematic diagram illustrating the wireless communication direction in a state of being inserted into the ear.

Referring to FIG. 4A, an antenna unit 1313 is formed in a first region 1110 of the first body 1100. A first module 1310 among a plurality of modules disposed inside the first region 1100 is formed. The antenna unit 1313 is formed on one surface of the first module 1310 facing the second body 1200. The battery unit 1340 is disposed on the one surface of the first module 1310 and the battery unit 1340 and the antenna unit 1313 are covered by the second body 1200.

The antenna unit 1313 may be formed of a metal pattern surrounding the battery unit 1340. The shape of the antenna unit 1313 is not limited to that shown in the drawings. The direction d shown in FIG. 4A is the radial direction of the antenna unit 1313.

Referring to FIGS. 2 and 4B, when the second region 1120 is inserted into the ear, one region of the first region 1100 is exposed to the outside. Particularly, the antenna unit 1313 disposed at the end of the first region 1100 is not inserted into the ear. Therefore, the antenna unit 1313 can perform wireless communications without being affected by the ear.

Further, as shown in FIG. 4B, the antenna unit 1313 may be preferably formed in a region of the second region 1120 that is distant from the auricle in a state where the second region 1120 is inserted into the ear. Accordingly, since the antenna unit 1313 radiates to the front of the ear, the wireless communication performance of the antenna unit 1313 may not affect the temperature sensor unit even when the temperature sensor unit is mounted on the ear.

Figure 5A:
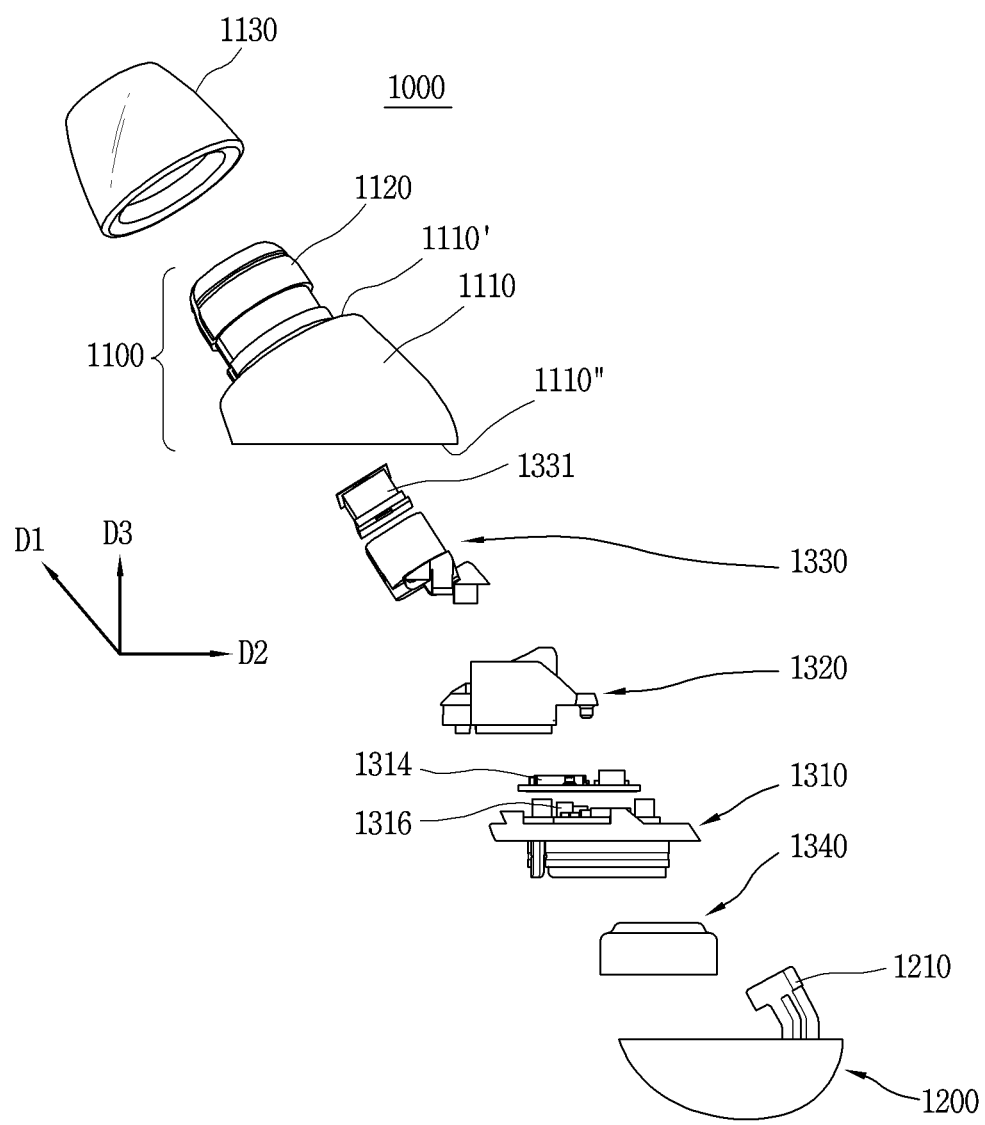
FIGS. 5A to 5C are conceptual diagrams illustrating a plurality of modules arranged in a first body.
Figure 5B:
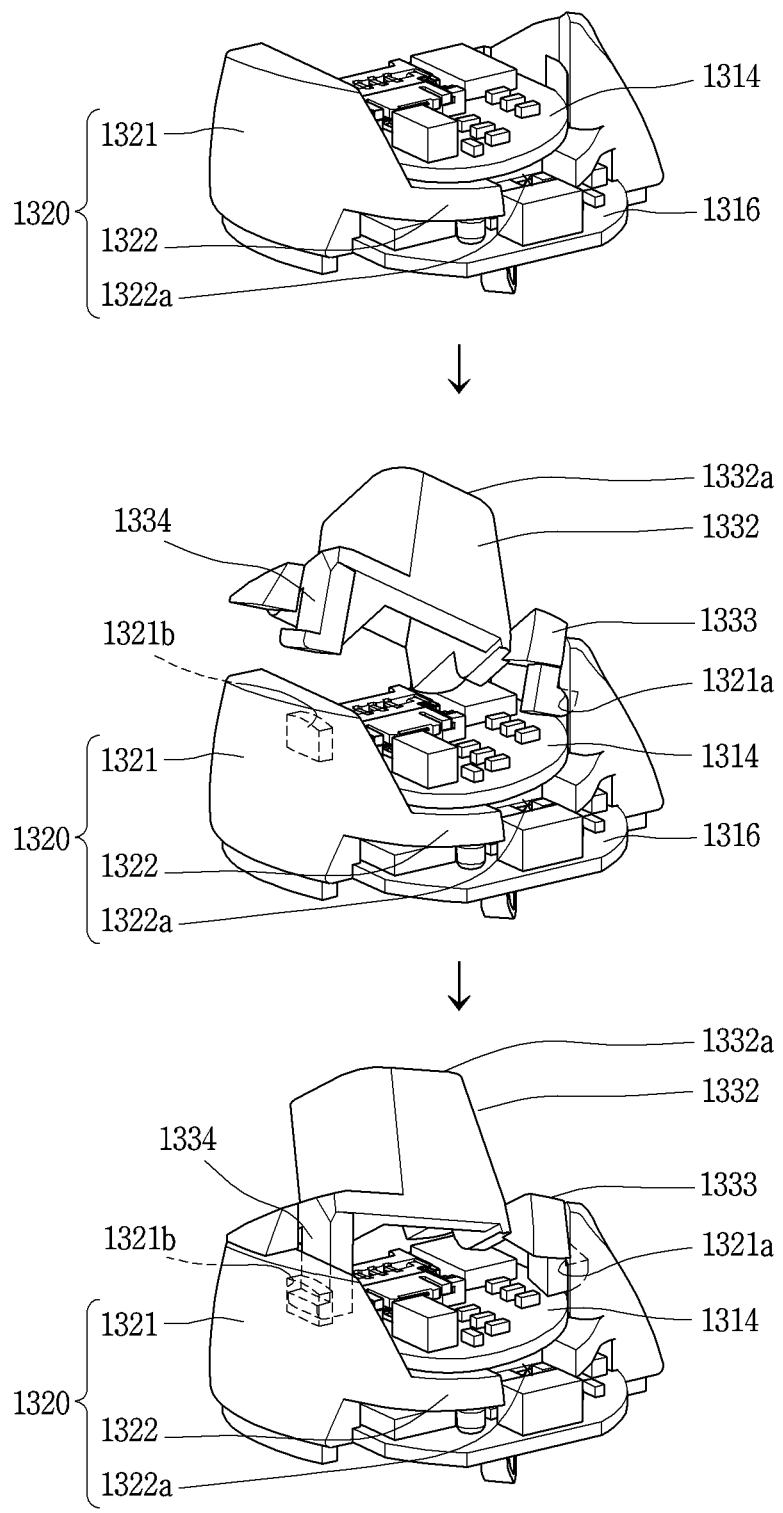
Figure 5C:
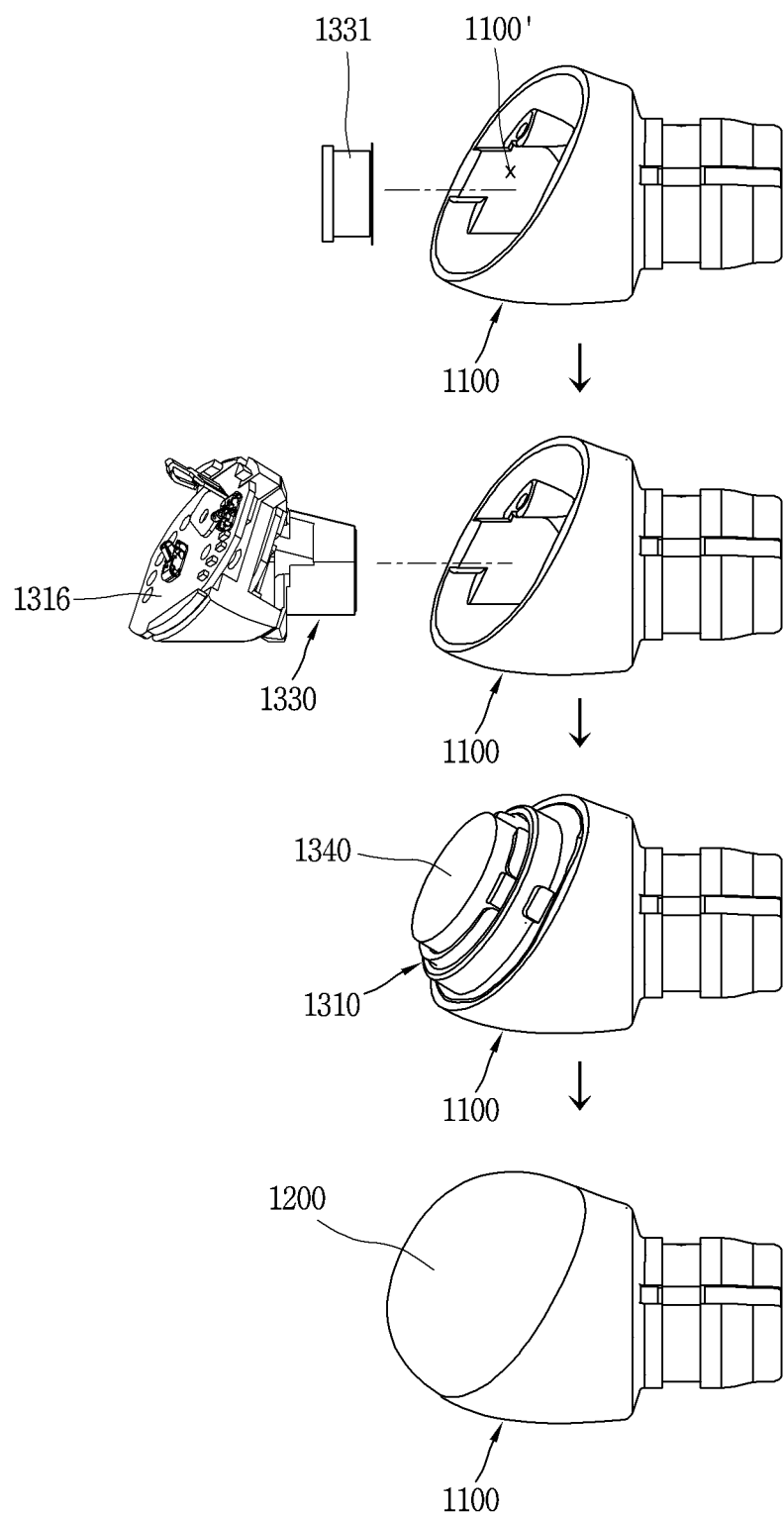

FIGS. 5A to 5C are schematic diagrams illustrating a plurality of modules arranged in the first body.

Referring to 5A, the temperature sensor device 1000 includes a first body 1100, a second body 1200, and a rubber cap 1130 mounted on the first body 1110. The temperature sensor device 1000 also includes first to third modules 1310, 1320, and 1330 mounted on the body 1100 and a battery unit 1340.

The second region 1120 extends from the one end 1100 of the first region 1100 along the first direction D1. The first region 1100 extends along the first direction D1. However, the other end 1100 of the first region 1100 is formed along the second direction D2 intersecting the first direction D1. The sections of the one end 1100 and the other end 1100 are formed in a direction intersecting each other. Accordingly, the second body 1200 is mounted on the other end 1100 of the first region 1100 in a third direction D3 intersecting the first and second directions D1 and D2. That is, distances from the other end 1100 to the second region 1120 are different from each other.

The first to third modules 1310, 1320, and 1330 are sequentially mounted on the first area 1110 and the second area 1120.

The first module 1310 is mounted on the first region 1110 of the first body 1100 to the second body 1200. The outermost surface of the first module 1310 corresponds to the other end 1100 of the first body 1100 having a shape cut in the second direction D2. The other end 1100 of the first region 1100 is covered by the first module 1310.

First and second circuit boards 1314 and 1316 are disposed on a first surface of the first module 1310. The first and second circuit boards 1314 and 1316 are arranged so that their at least one area is overlapped with each other. A receiving region for receiving the battery unit 1340 is formed on the second surface of the first module 1310. The side wall portion is protruded to form the accommodating region. The side wall part may include a spiral structure to be fixed to the second body 1200.

The battery unit 1340 and the temperature sensor 1331 are electrically connected by the first and second circuit boards 1314 and 1316.

The second module 1320 is mounted on a first surface of the first module 1310 and formed to surround a peripheral region of the first and second circuit boards 1314 and 1316. That is, the first and second circuit boards 1314 and 1316 are protected by the first module 1310.

Referring to FIG. 5B, the second module 1320 includes side wall portion 1321 corresponding to the inner surface of the first region 1110 and a supporting portion 1322 disposed between the side wall portions for supporting between the two circuit boards 1314 and 1316. The supporting portion 1322 includes an opening region 1322a for electrically connecting the first and second circuit boards 1314 and 1316.

The side wall portion 1321 is formed to correspond to the inner surface of the first region 1110 whereby the width and the degree of the tilt of the side surface can be formed to vary. The third module 1330 is mounted on one end of the second module 1320 and the first module 1310 is mounted on the other end of the second module 1320.

The third module 1330 includes a sensor supporting portion 1332 disposed in the first direction D1 and first and second fixed hook portions 1333 and 1334 extending from the sensor supporting portion 1332 to face each other.

The third module 1330 is disposed inside the second region 1120 extending in the first direction D1 and supports the temperature sensor 1331. One end of the third module 1330 may be a supporting surface 1332a for supporting the temperature sensor 1331.

The first and second fixed hook portions 1333 and 1334 have different lengths and have a hook structure in which an end portion can be inserted into a groove. Respective hook structures of the first and second fixed hook portions 1333 and 1334 are opposite to each other.

First and second fixing recesses 1321a and 1321b are formed on the inner surface of the second module 1321 so that the respective hook structures of the first and second large fixed hook portions 1333 and 1334 are fitted. The first and second fixing recesses 1321a and 1321b may be disposed adjacent to the first circuit board 1314. Accordingly, when the first and second fixed hook large portions 1333 and 1334 are inserted into the first and second fixing recesses 1321a and 1321b, the first circuit board 1314 is supported by the first and second fixed hook portions 1333 and 1334 to thereby prevent the first circuit board 1314 from moving. The first and second fixing recesses 1321a and 1321b are formed to face each other.

The first fixing hook portion 1333 having a relatively short length is first inserted into the first fixing recess 1321a and then the second fixing hook portion 1334 is inserted into the second fixing groove 1321b.

The lengths of the first and second fixed hook portions 1333 and 1334 may be different from each other. The length of the second fixing hook 1334 may be longer than the length of the first fixing hook 1333. Accordingly, the sensor supporting portion 1332 is inclined with respect to the first circuit board 1314 (and the other end 1110 of the first region 1110). Specifically, when the first and second fixed hook portions 1333 and 1334 are fixed to the first and second fixing recesses 1321a and 1321b, the side where the first fixed hook portion 1333 is tilted further downward due to the difference of the lengths of the first and second fixed hook portions 1333 and 1334. Accordingly, the sensor supporting portion 1332 can be arranged in the first direction D1.

Referring to FIG. 5C, a method of assembling the first to third modules and the first and second bodies is described.

The temperature sensor 1331 is inserted into the first body 1100. The temperature sensor 1331 is seated at the end of the second region 1120 of the first body 1100. The second and third modules 1320 and 1330 coupled as shown in FIG. 5B in a state where the temperature sensor 1331 is disposed in the second region 1120 are inserted into to the first body 1100. The second and third modules 1320 and 1330 are inserted such that the sensor supporting portion 1332 supports the temperature sensor 1331. The first and second circuit boards 1314 and 1316 are mounted on the second module.

The first module 1310 is inserted into the third module 1330 inserted in the first region 1110 of the first body 1100. The battery unit 1340 is inserted into the receiving region of the first module 1310. The battery unit 1340 may be detached from the first module 1310.

The second body 1200 is fixed to the first body 1100 so as to cover the battery unit 1340. Referring to FIG. 5A, the second body 1200 includes a fixing protrusion 1210 inserted and fixed in one region of the first body 1100. The fixing protrusion 1210 is movably fixed to the first body 1100 so that the fixing protrusion 1210 is fixed even when the second body 1200 is detached from the first body 1100. Accordingly, since the second body 1200 is connected to the first body 1100, it is possible to prevent the second body 1200 from being lost.

Figure 5D:
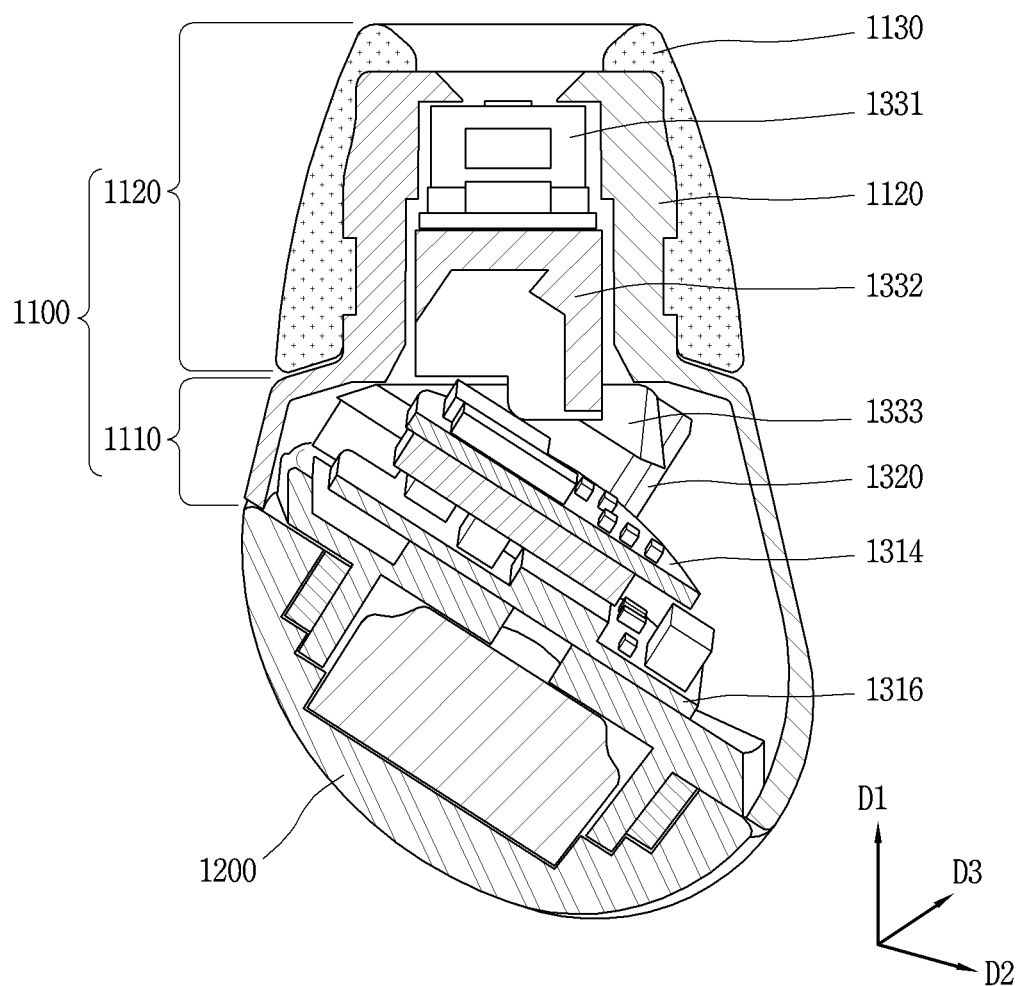
FIG. 5D is a conceptual diagram illustrating an arrangement structure of first to third modules.

FIG. 5D is a schematic diagram illustrating the arrangement structure of the first to third modules.

The first body 1100 and the second body 1200 have a shape extending in one direction (first direction D1) and the temperature sensor 1331 is disposed in the second region 1120 of the first body 1100 in the first direction D1.

Therefore, the temperature sensor 1331 may have a sensing range of a specific angle with respect to the first direction D1

In the first region 1110 of the first body 1100, the first and second circuit boards 1314 and 1316 are arranged in a second direction D2 that intersects with the first direction D1. The first and second circuit boards 1314 and 1316 are disposed in the second direction D2 in a space defined by the first and second bodies 1100 and 1200 to thereby secure a maximum width. Accordingly, it is possible to dispose the circuit board having the largest width while being disposed in the inner space of the first and second bodies 1100 and 1200.

The first and second bodies 1100 and 1200, which constitute an external appearance of the temperature measuring device according to the present invention, have a shape extending along one direction, one region of which is inserted into the ear canal and the other region of which does not have such structure as covering or fitting to the outside of the ear. That is, because the volume of the uninserted region is minimized, when worn on the ear (particularly when sleeping with the temperature measuring device worn on the ear), the region of contact with or supported by the outer structure of the ear is minimized. Thus, the feeling of wearing can be improved.

Further, by arranging the circuit board obliquely with respect to the one direction, a volume of the circuit board can be secured to thereby secure the stability of the driving of the temperature sensor and realize additional functions.

The temperature sensors can be arranged in the direction adjacent to the eardrum using the first and second fixed hook portions having different lengths with respect to the obliquely arranged circuit board. Accordingly, the body temperature of the region adjacent to the eardrum can be accurately measured and the circuit board can be obliquely arranged to realize a structure extending in one direction, thereby improving comfort when the eardrum is mounted on the ear.

Referring back to FIG. 1D, since the region where the eardrum (tm) is disposed is included within the sensing range of the temperature sensor of the thermometer 1000 inserted in the external ear canal (EAM), accurate measurement is possible. Further, because the thermometer is stably fixed in the ear canal, it is possible to prevent errors in measurement of the body temperature due to movement or measurement posture.

Figure 6:
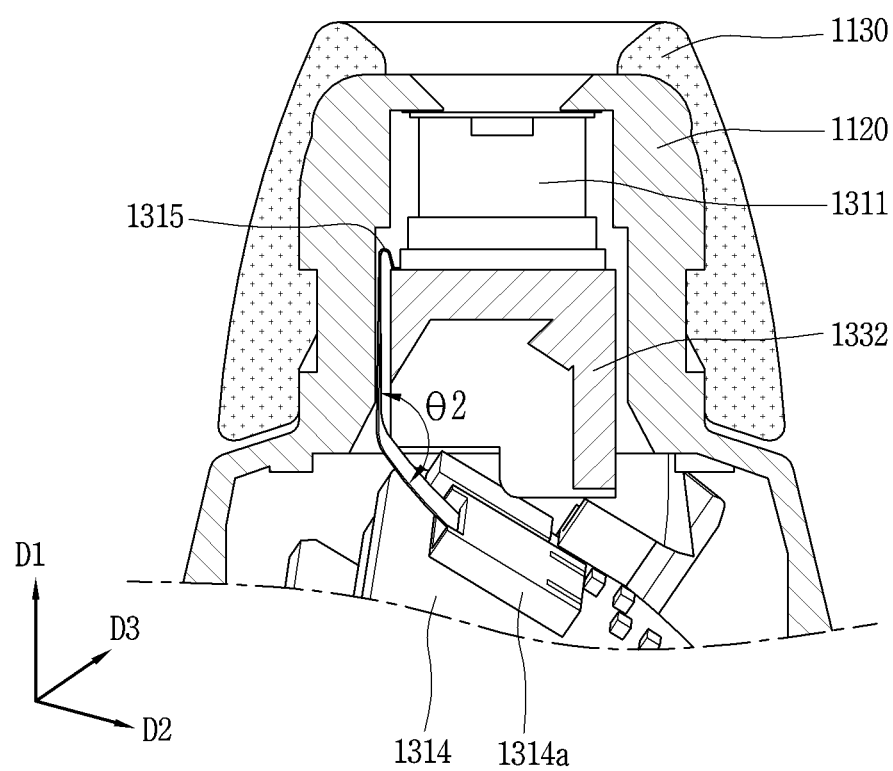
FIG. 6 is a conceptual diagram illustrating an arrangement of a flexible circuit board.

FIG. 6 is a schematic diagram illustrating the arrangement of a flexible circuit board.

The temperature sensor 1311 is electrically connected to the first circuit board 1314 by a flexible circuit board 1315. Meanwhile, the sensor supporting portion 1332 and the temperature sensor 1311 are disposed in the first direction D1 and the first circuit substrate 1314 is disposed in the second direction D2 intersecting with the first direction D1.

Referring to FIGS. 5B and 6 together, one region of the first circuit board 1314 adjacent to the relatively short first fixed hook portion 1333 is disposed adjacent to the temperature sensor 1311. Accordingly, one end of the flexible circuit board 1315 is connected to the temperature sensor 1311 and the other end thereof is connected to one region of the first circuit board 1314. That is, the flexible circuit board 1315 is connected to a region of the first circuit board 1314 adjacent to the first fixed hook portion 1333. The first circuit board 1314 may include a terminal portion 1314*a* which is disposed in the one region and connected to the flexible circuit board 1315.

The flexible circuit board 1315 connected to the one region of the first circuit board 1314 is bent by an angle θ2 between the first and second directions D1 and D2. Therefore, the degree of bending of the flexible circuit board 1315 can be minimized.

FIGS. 7A to 7E are schematic diagrams illustrating a structure for coupling and separating the second body.

Figure 7A:
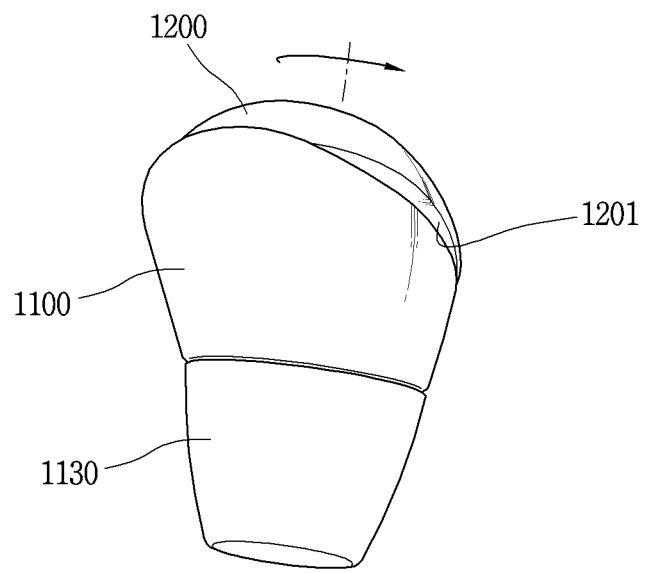
FIGS. 7A to 7E are conceptual diagrams illustrating a structure for coupling and decoupling a second body.

Referring to FIG. 7A, the second body 1200 is separated from the first body 1100 by rotation of the second body 1200 with respect to the first body 1100. The second body 1200 includes a nail groove 1201 which forms a space with respect to the first body 1100. In this case, the user can separate the second body 1200 from the first body 1100 using the nail groove 1201.

However, the second body according to one embodiment may not include the nail groove 1201.

Figure 7B:
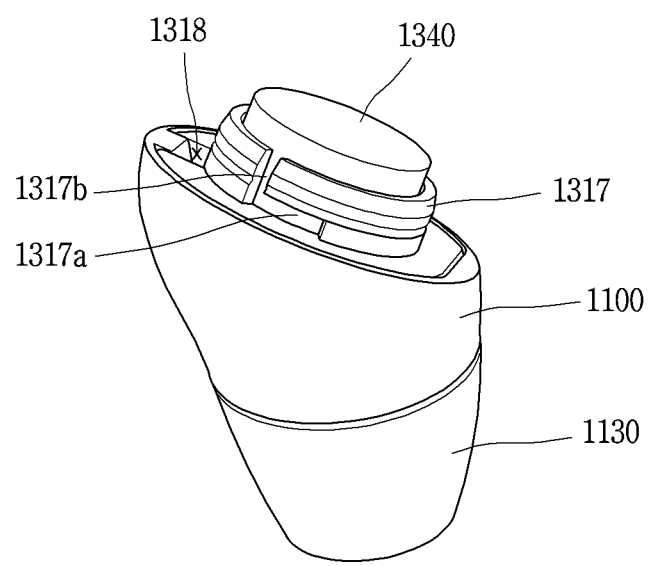
Figure 7C:
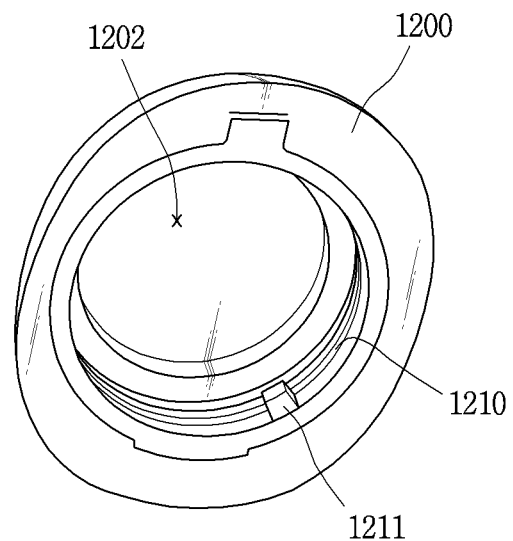

Referring to FIGS. 7B and 7C, the first module 1310 includes a side wall portion 1317 for forming a receiving region for receiving the battery unit 1340. The side wall portion 1317 is formed to surround the battery unit 1340. The outer surface of the side wall portion 1317 is formed with a thread. Meanwhile, the second body portion 1200 includes an inner region 1202 which surrounds the side wall portion 1317 and accommodates the battery unit 1340. A screw thread 1210 corresponding to the thread of the side wall portion 1317 is formed on the inner surface of the second body portion 1200 forming the inner region 1202.

The side wall portion 1317 and the second body portion 1200 may be fixed by rotation. Meanwhile, the side wall portion 1317 includes a guide groove 1317*a* which is formed along the outer circumference of the side wall portion 1317 and a fixing groove 1317*b* extending in the other direction from the end of the guide groove 1317*a*. Meanwhile, the second body portion 1200 includes a protrusion 1211 protruding from the inner surface of the inner region 1202. The protrusion 1211 moves along the guide groove 1317*a* so that the first and second body portions 1100 and 1200 rotate relative to each other. The protrusion 1211 moves along the guide groove 1317*a* and is seated in the fixing groove 1317*b* so that the first and second body portions 1100 and 1200 are fixed.

Figure 7D:
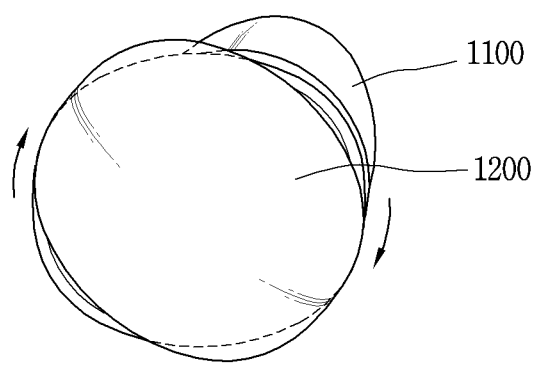

As shown in FIG. 7D, the second body portion 1200 may be separated from the first body portion 1100 by rotating about the first body portion 1100. When the second body portion 1100 is separated from the first body portion 1100, the battery unit 1340 is exposed. The battery unit 1340 is separated from the first body unit 1100 and may be a detachable-type battery.

Figure 7E:
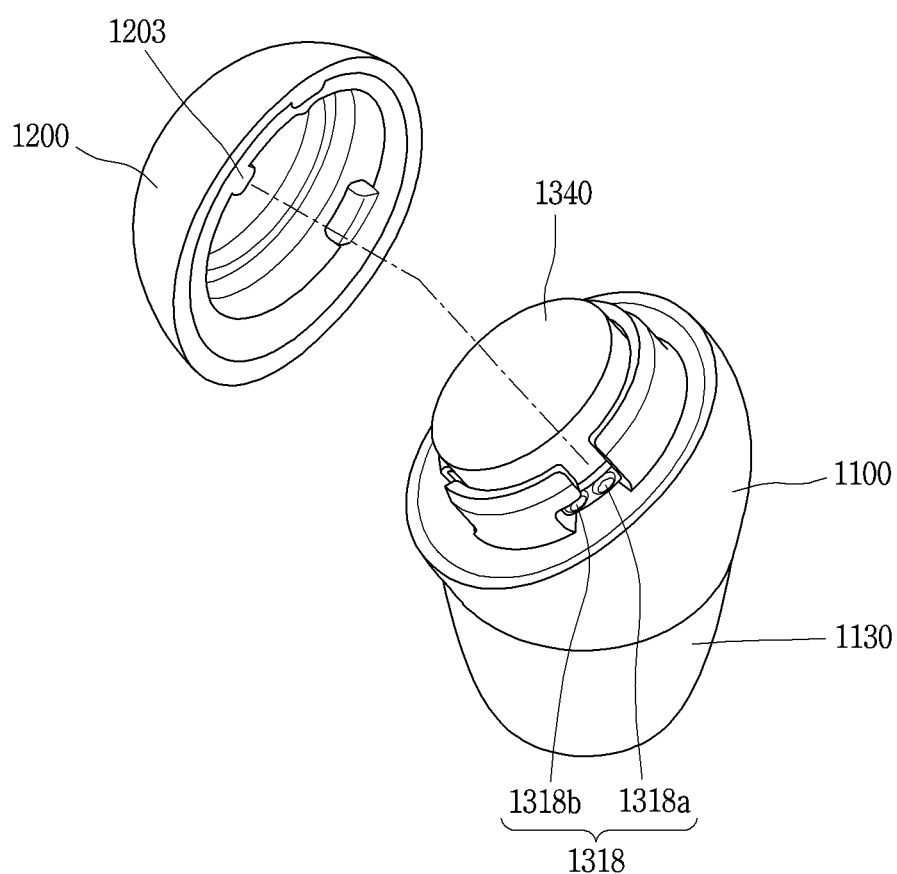

Referring to FIG. 7E, the second body portion 1200 includes a locking protrusion 1203, and the first body portion 1100 includes a locking groove portion 1318 formed to catch the locking protrusion 1203. The locking groove portion 1318 includes first and second grooves 1318*a* and 1318*b*. The locking protrusion 1203 moves along the first groove 1318*a* while the second body portion 1200 fits in the first body portion 1100.

The second groove 1318*a* is formed to extend from the end of the first groove 1318*a*. The first and second grooves 1318*a* and 1318*b* are formed in directions intersecting with each other. The locking protrusion 1203 fitted in the first groove 1318*a* is fitted into the second groove 1318*b* by the rotation of the second body portion 1200. The second body portion 1200 is not separated from the first body portion 1100 when the second body portion 1200 is fitted in the second groove 1318*b*.

Accordingly, the second body portion 1200 is fitted in the direction in which the first groove 1318*a* is formed, and rotates in a specific direction (counterclockwise) so that the locking protrusion 1203 is fitted into the second groove 1318b and thus the locking protrusion 1203 is fixed to the first body portion 1100.

Figure 8A:
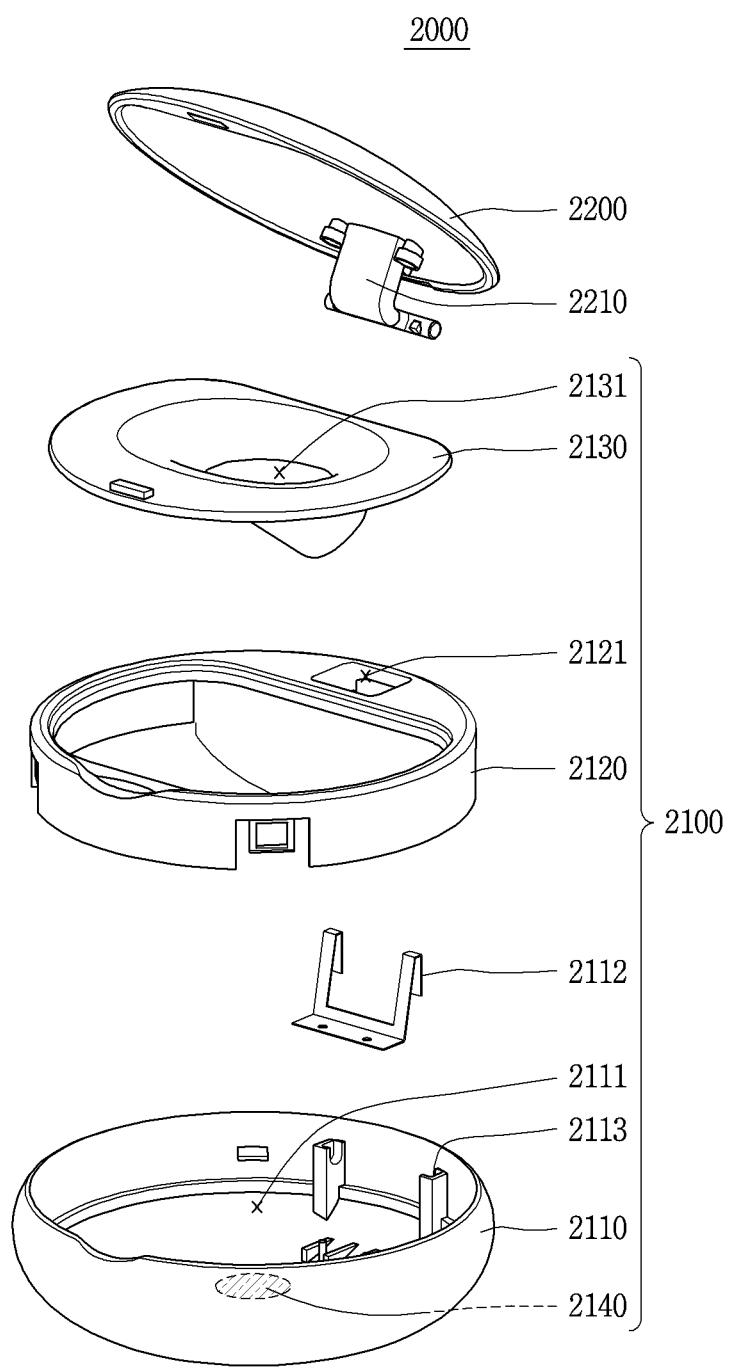
FIG. 8A is an exploded view illustrating components of a receiving device.
Figure 8B:
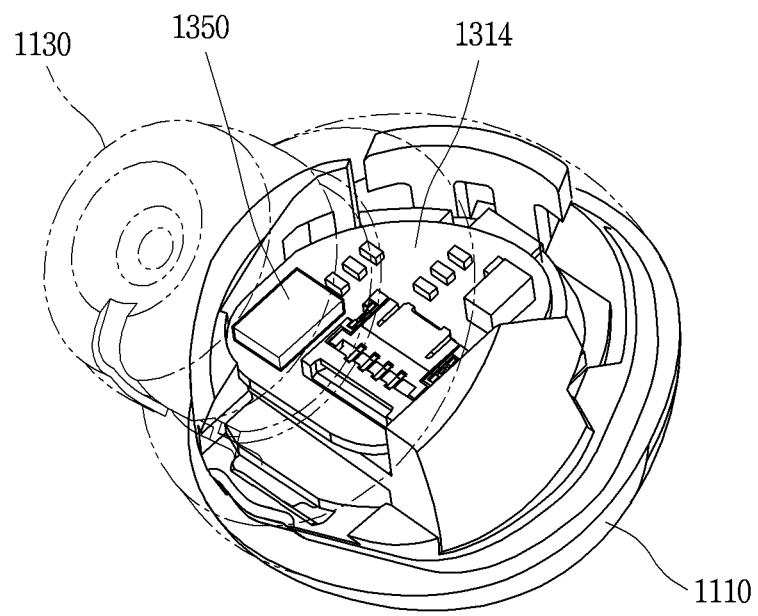
FIGS. 8B and 8C are conceptual diagrams illustrating a hall sensor for sensing that a temperature measuring device is mounted on the receiving device, and a magnet unit.
Figure 8C:
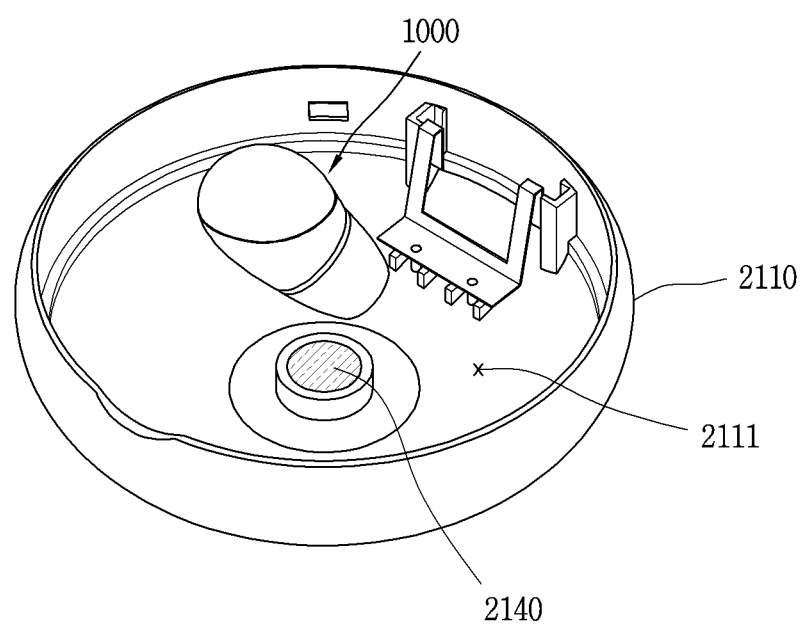

FIG. 8A is an exploded view illustrating components of a receiving device, and FIGS. 8B and 8C are schematic diagrams illustrating a hall sensor and a magnet unit for detecting the mounting of a temperature measuring device on a receiving sensor.

Referring to FIG. 8A, the receiving device 2000 includes the body portion 2100, the lid portion 2200 and a connection portion 2210 connecting the lid portion 2200 to the body portion 2100.

The body portion 2100 includes a first body 2110 constituting an outer appearance and forming an inner space 2111, a second body 2120 mounted on the inner space 2111 and a third body 2130 including a receiving region for seating the thermometer 1000 therein. The third body 2130 is inserted into the second body 2120.

A magnet unit 2140 is disposed inside the first body 2110. Further, a spring 2112 for connecting the connection portion 2210 and a fixing portion 2113 to which the spring is fixed may be disposed inside the first main body 2110.

The second body 2120 includes an opening 2121 which is stored in the first body 2110 and through which the spring 2112 can pass. The spring 2112 passes through the opening 2121 and is fixed to the connection portion 2210.

Meanwhile, a region distinguished from the region where the opening 2121 is formed is formed with a recessed portion. The magnet unit 2140 is covered by a region where the recess portion is formed. The third body 2130 is disposed in the recess portion. The body 2130 includes a receiving region 2131 for seating the thermometer 1000 therein and the receiving region 2131 may have a recessed shape for enclosing one region of the thermometer 1000. The receiving region 2131 is formed in one region overlapping with the magnet unit 2140.

Referring to FIG. 8C, when the thermometer 1000 is seated in the receiving region 2131, the thermometer 1000 is disposed adjacent to the magnet unit 2140.

Meanwhile, the thermometer 1000 further includes a hall sensor 1350 disposed on the first circuit board 1314 (or the second circuit board 1316). The hall sensor 1350 senses a magnetic change. The thermometer 1000 can determine whether the thermometer 1000 is seated in the receiving device 2000 based on the magnetic change sensed by the hall sensor 1350. In this case, the second region 1120 may be received while being inserted into the receiving region 1231 so that the hall sensor 1350 is adjacent to the magnet unit 2140 and the second region 1120 of the first body 1100 is adjacent to the magnet unit 2140.

For example, when the thermometer 1000 is stored in the receiving unit 2000, that is, when the magnet unit 2140 is detected as being adjacent to the hall sensor 1350 according to a magnetic change detected by the hall sensor 1350, the power of the thermometer 1000 can be turned off. On the contrary, when the hall sensor 1350 does not detect a magnetic change, the thermometer 1000 can be turned on.

In this case, the thermometer 1000 may not include a switch or the like for controlling the power supply, so that the volume of the thermometer 1000 can be minimized.

The power supply is turned off when it is mounted on the receiving unit 2000 but it is not used, thereby increasing the battery life.

Further, the thermometer 1000 may transmit the body temperature information to an external device when it is sensed that the magnetic change of the hall sensor 1350 is sensed and stored in the receiving unit 2000. In this case, when the thermometer 1000 is inserted into the user's ear, limitation of the wireless communication can minimize the body effect due to the communication.

Further, although not specifically shown in the figures, the receiving device 2000 may further include a dehumidifying agent stored in the inner space. The dehumidifying agent may be composed of a silica gel which absorbs moisture. The dehumidifying agent can be reused by heating it in a microwave oven. Further, the receiving device 2000 may include a cleaning tool for removing foreign substances such as earwax of the body temperature from the thermometer 1000.

Figure 9A:
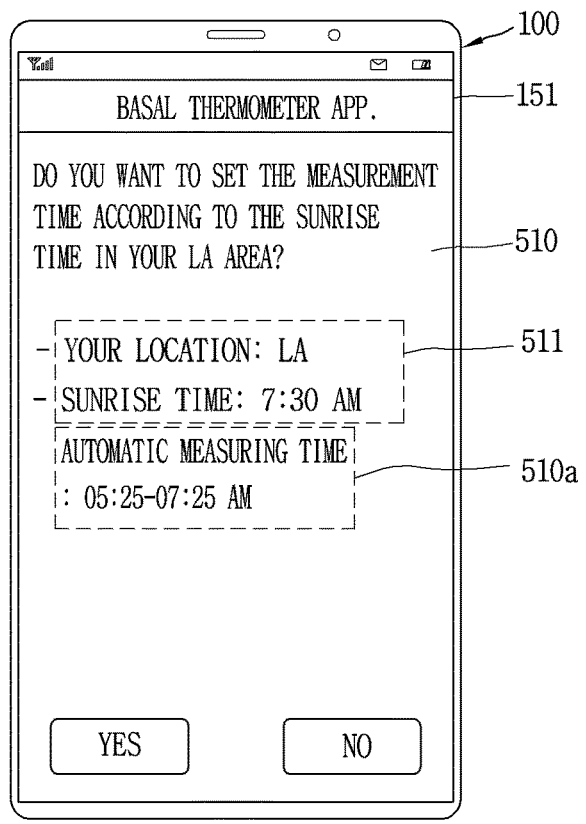
FIGS. 9A and 9B are conceptual diagrams showing a setting screen for setting a measurement time.
Figure 9B:
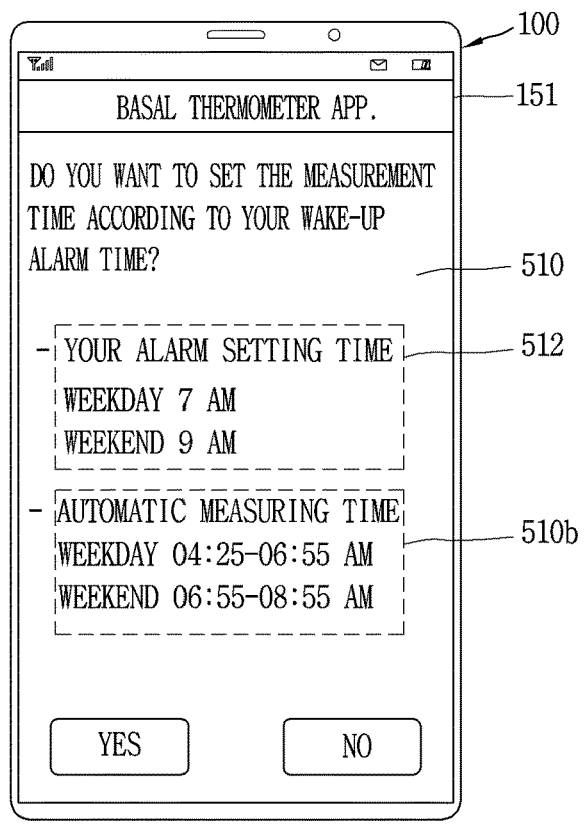

FIGS. 9A and 9B are schematic diagrams showing a setting screen for setting a measurement time.

The thermometer 1000 according to an embodiment of the present invention is cooperates with an external device (for example, a mobile terminal 100). The antenna unit 1313 performs a measurement function in conjunction with the external device 100 or transmits the measured data to the external device 100. Meanwhile, the thermometer 1000 may further include a memory for storing the measured data.

The thermometer 1000 is controlled to start measurement at a time set by the external device 100 and to measure the body temperature at a predetermined cycle. The thermometer 1000 can measure the temperature several times in the sleep state corresponding to the 3-4 steps of non-REM sleeping which is the most stable sleeping state. The external device 100 may form body temperature data as an average value of the body temperature information measured during the specific time.

The thermometer 1000 receives a control command to start body temperature measurement at a time set by the external device 100. The control of the body temperature measurement can be set by the user.

The day with the lowest basal body temperature during the menstrual cycle is considered to be the day of ovulation. In addition, if the basal body temperature is maintained at a high temperature for 18 days or more after the ovulation day, it is considered that there is a possibility of pregnancy. If the high temperature is increased without being maintained, it is considered that the menstruation starts. Here, the basal body temperature corresponds to the lowest body temperature that appears in the most stable state everyday. The basal body temperature is low from evening, lowest before the sunrise and then increases again.

Referring to FIG. 9A, the measurement time of the thermometer 1000 may be set by a sunrise time according to a user's location. The external device 100 may sense the location of the user (i.e., the location of the external device 100) by a location information sensing unit (e.g., GPS).

The display unit 151 of the external device 100 outputs a first setting screen 510 for setting the measurement time. The first setting screen 510 may be output when the application for executing the body temperature measurement function is executed for the first time, when the measurement start time is not set and so on.

The first setting screen 510 includes the sunrise information 511 according to the location information of the external device 100 and the information 510a about the measurement start time calculated according to the sunrise information. The measurement start time may be set to two hours before the sunrise time. Therefore, the temperature can be measured in the most stable non-REM sleep 3-4 steps 2 hours before the user's wake-up.

Referring to FIG. 9B, the first setting screen 510 includes pre-stored alarm time information 512 and information 510b about a measurement start time calculated based on the alarm time information.

When there is alarm time information stored by the user, a controller of the external device 100 may set the measurement start time to two hours before the alarm time.

Although not shown in the figure, the measurement start time can be set based on the touch input applied to the first setting screen 510. Alternatively, the residential region information or the alarm time may be changed. In addition, the measurement start time can be input using the first setting screen 510. In this case, the display unit 151 may output guide information that the measurement start time is preferably 3 hours to 4 hours after sleeping or 2 hours before the wake-up.

In addition, the controller of the external device may execute the positioning application or the alarm time setting application on the first setting screen 510.

Accordingly, even if the user does not set the measurement start time separately, the user can predict the sleeping time of the user according to the necessary information and recommend the measurement start time.

Figure 9C:
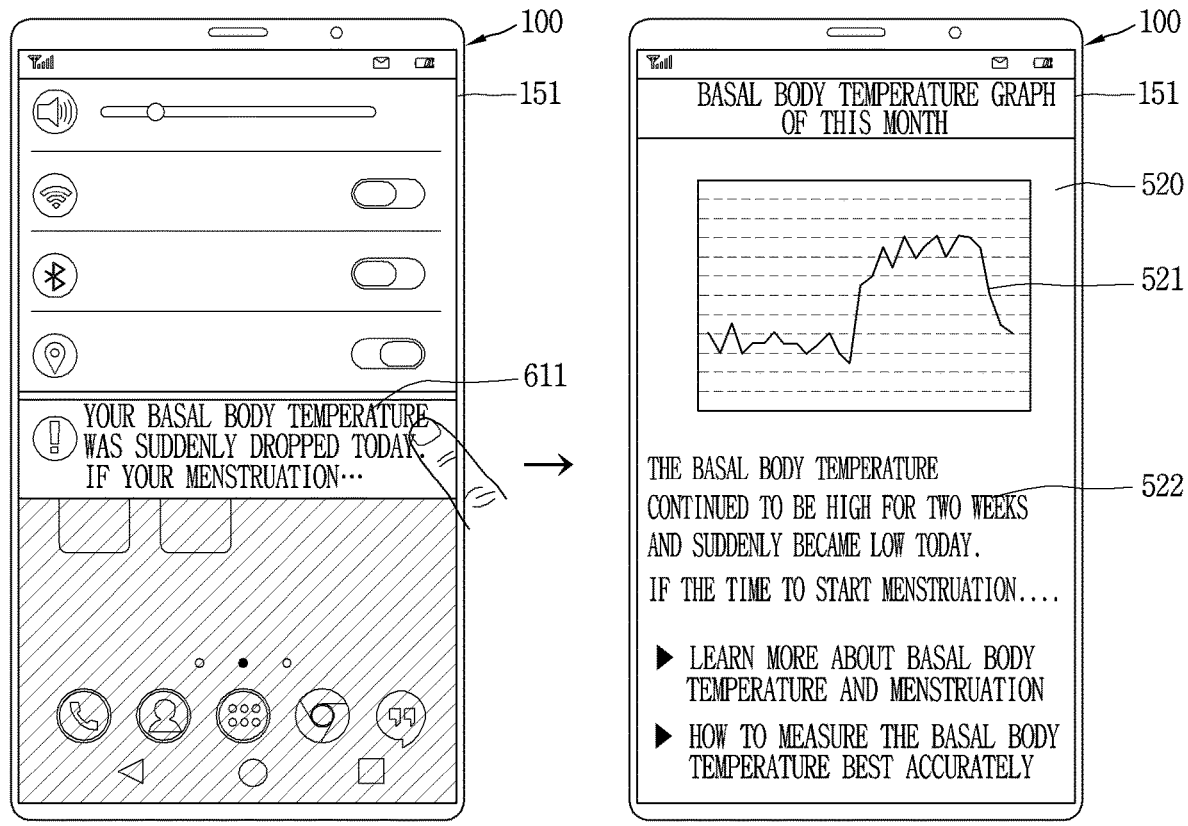
FIGS. 9C and 9D are conceptual diagrams illustrating a control method of outputting notification information based on a sensed body temperature.
Figure 9D:
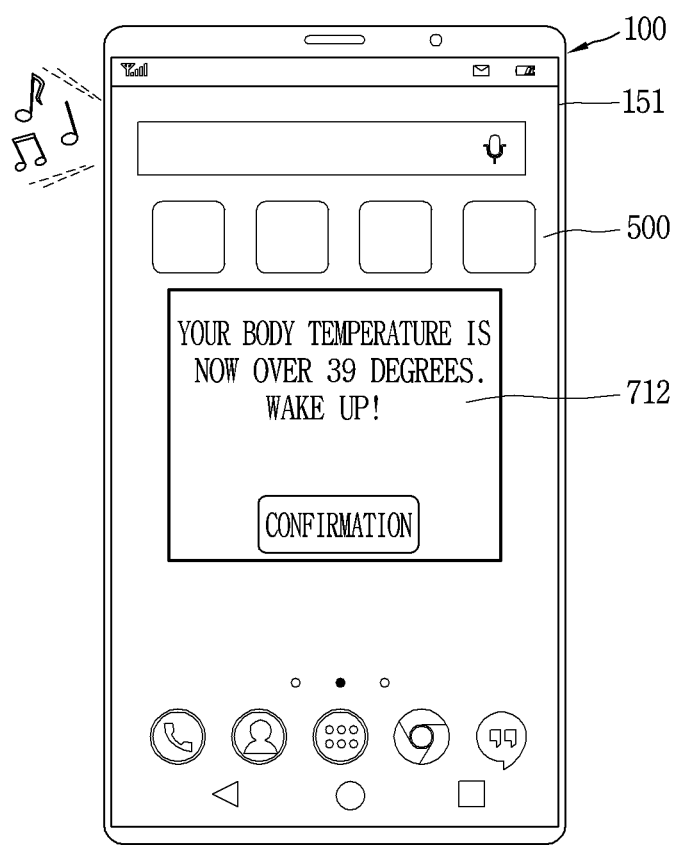

FIGS. 9C and 9D are schematic diagrams illustrating a control method of outputting notification information based on sensed body temperature.

The thermometer 1000 according to the present invention transmits and receives measured body temperature information while performing wireless communication with the external device 100. The external device 100 forms body temperature data using the received body temperature information and forms guide information according to a change in body temperature.

For example, the controller of the external device 100 outputs the first notification information 611 when the body temperature suddenly drops. The first notification information 611 may include analysis result information indicating that the menstruation is expected to start. The analysis result information can output information that predict the ovulation when the low body temperature is measured, the start of the menstruation when the body temperature suddenly drops after the body temperature rises, and the pregnancy when the body temperature is maintained at the high temperature state. The first notification information 611 may be the form of text or image.

Alternatively, the external device 100 may output the first notification information 611 including information indicating measured body temperature data.

The controller executes an application related to the basal body temperature based on the touch input applied to the first notification information 611 and controls the display unit 151 to output the first result screen 520 of the application. The first result screen 520 may include a graph 521 indicating a change in body temperature, and a description unit 522 describing a change in body temperature.

Referring to FIG. 9D, the controller may output the second notification information 712 when the change in the body temperature is out of the normal range or when the body temperature itself is out of the range of the normal body temperature. The second announcement information 712 may be the form of pop-up window.

Also, while the second announcement information 712 is being output, the external device 100 may output a vibration or output specific auditory data. Accordingly, when an abnormality occurs in the body, the user can confirm it through the notification and take action.

Alternatively, when the change in the body temperature is out of the normal range or when the cycle of the basal body temperature is not clear, the controller may output guide information for recommending a visit to a hospital through the second notification information 712. Although not shown in the figure, when the touch input is applied to the second notification information 712, the application is executed and additional analysis information can be output on the execution screen.

Figure 10A:
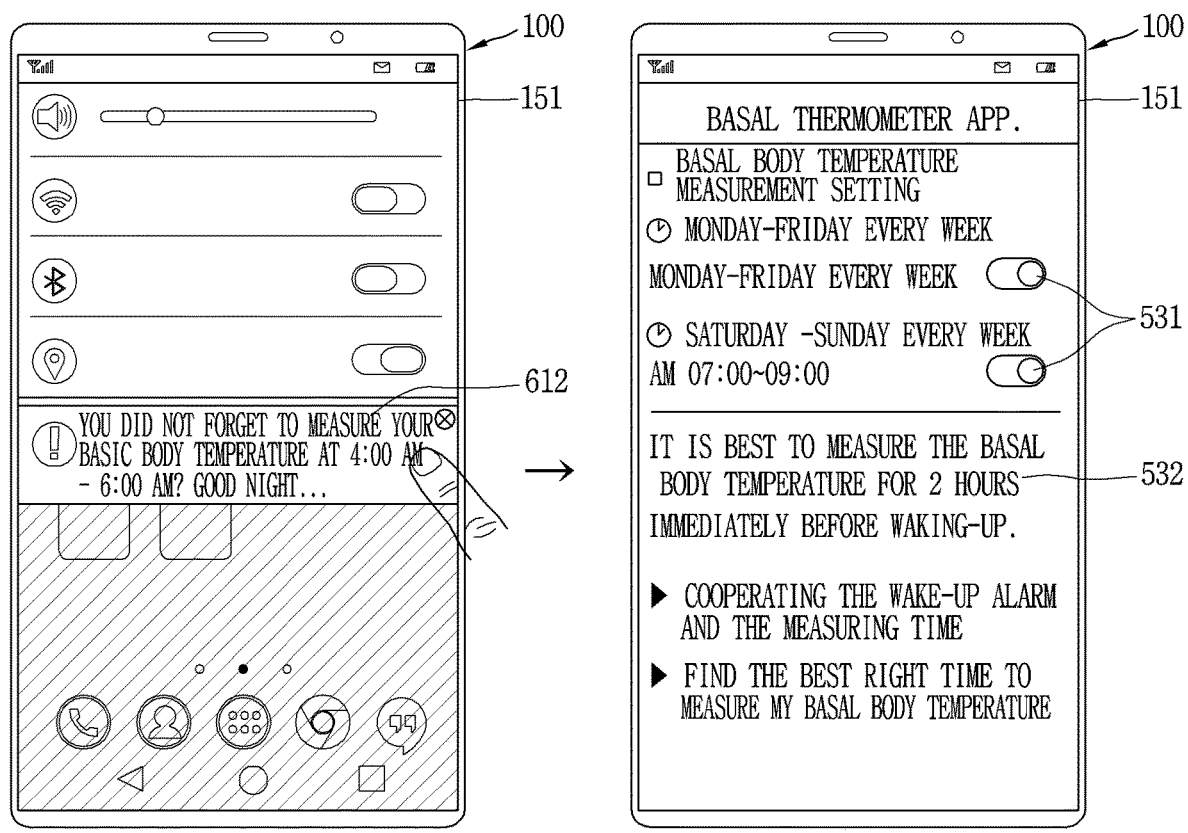
FIGS. 10A and 10B are conceptual diagrams illustrating a control method of outputting guide information for guiding a measurement.
Figure 10B:
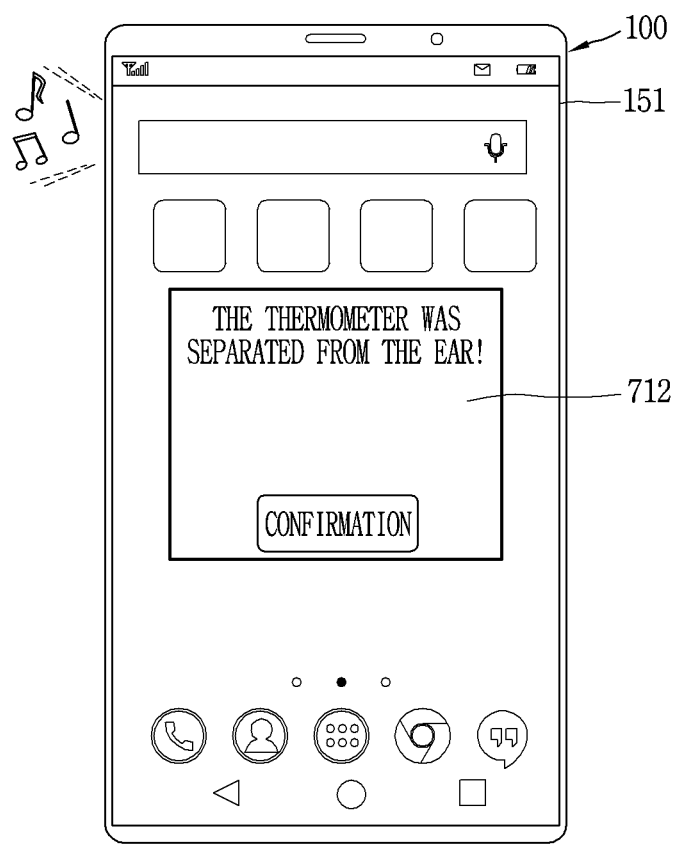

Referring to FIGS. 10A and 10B are schematic diagrams illustrating a control method of outputting guide information for guiding measurements.

Referring to FIG. 10A, the controller controls the display unit to output third notification information 612 including guide information recommending measurement of basal body temperature before sleeping. The third notification information 612 may be output together with information on the generated event and driving information of the external device 100.

The controller executes the application when the touch input is applied to the third notification information 612 and controls the display unit to output a setting screen 532 for measuring the body temperature. The setting screen 532 may include an icon 531 or the like for changing the setting of the basal body temperature measurement for each day of the week.

Referring to FIG. 10B, the controller senses that the thermometer 1000 has been separated from the user's ear when the body temperature information sensed during a predetermined time is out of a temperature range corresponding to the body temperature. In this case, the display unit 151 outputs fourth notification information 712 indicating that the thermometer has been separated from the ear. The fourth notification information 712 may be the form of pop-up window. Also, the external device 100 may output vibration or output audible data.

In addition, the controller may control the display unit to output guide information for guiding accurate wearing when abnormal body temperature information according to a certain criterion is received.

Meanwhile, the thermometer 1000 can transmit information on the remaining amount of the battery to the external device 100. When the remaining amount of the battery is less than the reference remaining amount, the thermometer 1000 may control the display unit to output the guide information.

In addition, even if the measurement is irregular or the accurate measurement continues, the result information on the measurement may be output on the display unit. Accordingly, the user can measure the body temperature more accurately based on the guide information, and can more accurately perform measurement later by feedback of the measured information.

Figure 11:
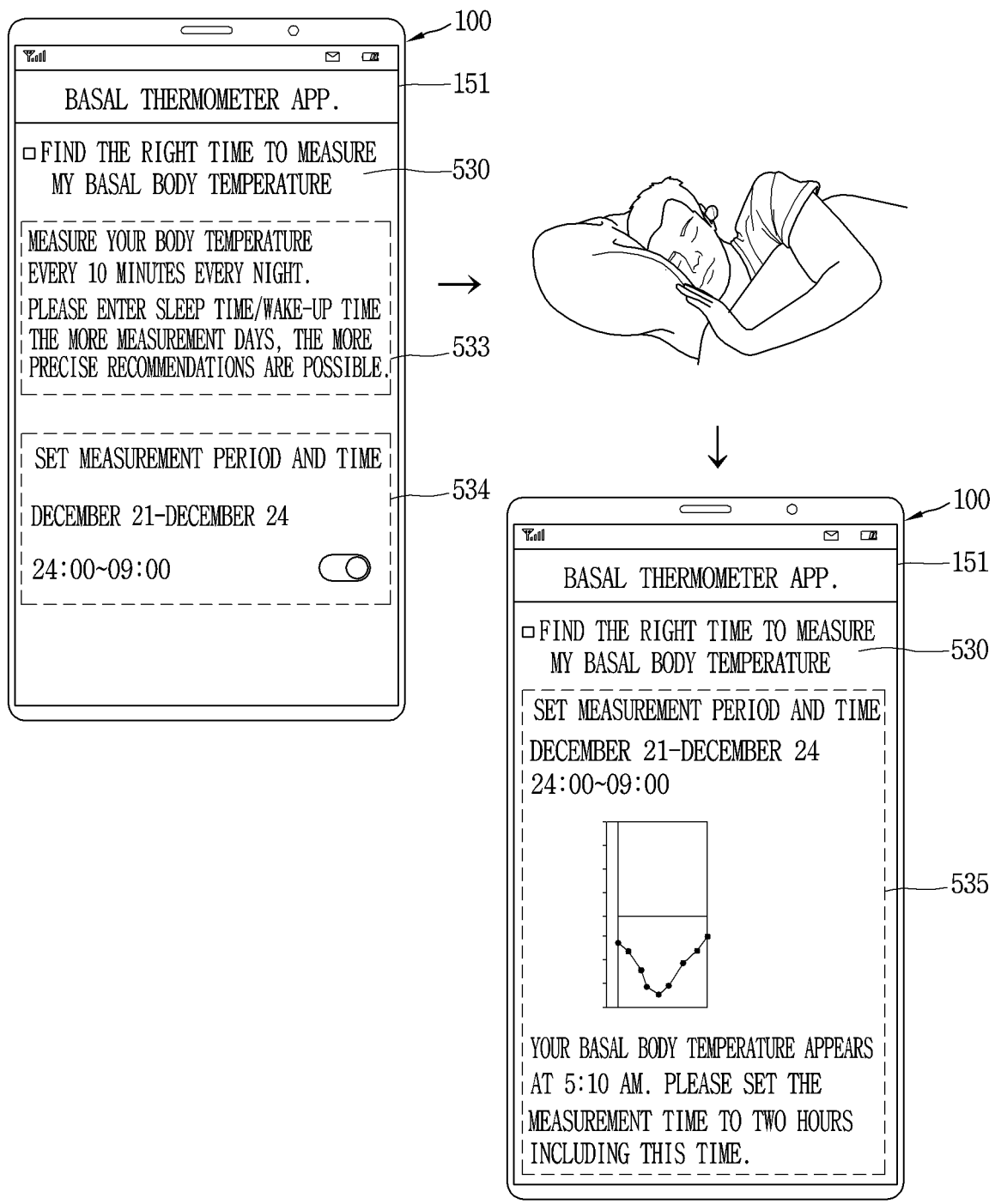
FIG. 11 is a conceptual diagram illustrating a control method for detecting an appropriate measurement start time according to an embodiment of the present invention.

FIG. 11 is a schematic diagram illustrating a control method for detecting an appropriate measurement start time according to an embodiment of the present invention.

Referring to FIG. 11, the display unit 151 outputs a measurement time detection screen 530. The detection screen 530 includes guide information 533 and a measurement period setting image 534. The thermometer 1000 measures a change in body temperature for a predetermined period of time and the external device 100 recommends the user to set a measurement start time around a time at which the lowest basal body temperature appears. Thus, the user can set the measurement start time for more accurate measurement.

The controller outputs a result image 535 based on the collected body temperature information. The resultant image includes recommended measurement time information for measuring a change in body temperature for a set specific period and a time when the lowest basal body temperature is indicated.

According to the present invention, the user is set to measure for 2 hours before waking up, and is set to measure every predetermined period of about 10 minutes. The average sleep cycle is 90 minutes, and the most stable non-REM 3 to 4 steps of the body temperature during it correspond to approximately 25 minutes. Therefore, if the body temperature is measured at intervals of 10 minutes, the body temperature can be measured in the non-REM 3-4 steps, which is the most stable sleeping phase even if the sleep cycle becomes irregular depending on the user's condition.

Figure 12:
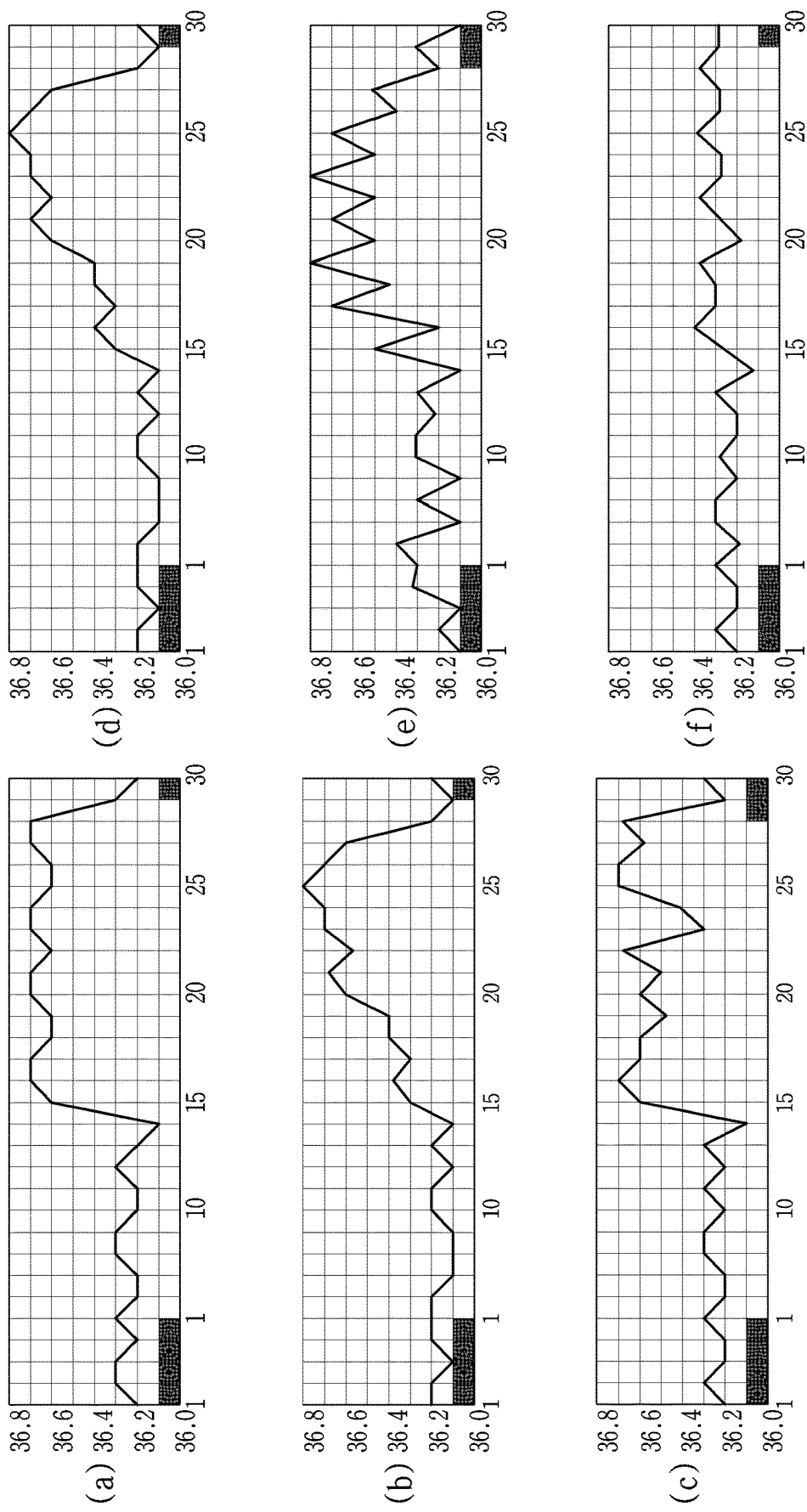
FIG. 12 is a conceptual diagram illustrating an example of a change in body temperature by menstrual cycles according to various states.

FIG. 12 is a schematic diagram illustrating an example of a body temperature change according to various states.

According to the present invention, the thermometer 1000 transmits body temperature information to the external device 100. For example, the thermometer 1000 may transmit information at the state stored in the receiving device 2000, transmit information when it is positioned adjacent to the external device 100 or transmit the body temperature information to the external device 100 in real time when the body temperature is measured. The external device 100 can form body temperature data using the received body temperature information and calculate the resultant information according to the body temperature data.

A graph of the general basal body temperature during the menstruation cycle is shown in (a) of FIG. 12. The low temperature period and high temperature period are repeated, and at the end of the low temperature period, the lowest temperature is recorded and enters the high temperature period. In this case, it is possible to output the notification information from the previous month-based next month's ovulation prediction day and two days before the predicted day of menstruation start.

A graph showing changes in body temperature when the body temperature rises for a long time after the low temperature period is shown in (b) of FIG. 12. If the rise of the body temperature is continued for a long time without showing any distinction after the low temperature period, the external device may output guide information recommending utilization of the ovulation test for more accurate confirmation of the ovulation date before the body temperature rise next month based on the previous month.

A body temperature sensing graph in which the high temperature is unstable is shown in (c) of FIG. 12. In this case, the external device 100 may output guide information for guiding the condition adjustment.

A case where the low-temperature period is long and the high-temperature period is short is shown in (d) of FIG. 12. It is considered to be a rare menstrual state when the entire menstruation cycle becomes longer than 60 days due to the long low-temperature period. In this case, the external device 100 may recommend utilization of the ovulation test before the rise of body temperature next month based on the previous month and may output guide information recommending the visit to a hospital.

A graph showing a change in body temperature measured in a sharp manner is shown in (e) of FIG. 12. In this case, the external device 100 may recommend the use of the ovulation test before the rise of body temperature next month based on the previous month and may output guide information for confirming ovulation mucus and ovulation pain.

A body temperature measurement graph in which the distinction between a low-temperature period and a high-temperature period is unavailable is shown in (f) of FIG. 12. In this case, if the variation width of the entire basal body temperature for a period of 2 months or more does not show any change in the predetermined temperature (0.2° C.), the external device 100 may determine that it is in a suspected state of no-ambulation, and may output guide information for guiding an examination at a hospital.

The controller of the external device may be used in case that the temperature of the basal body does not fall below the characteristic temperature (0.2° C.) even after 2-3 days from the start of menstruation, when the high-temperature period is maintained for 20 days or more after the ovulation date (the date when the basal temperature is the lowest), the controller outputs the recommended guide information. If the distinction between the low temperature and the high temperature is impossible, the child outputs guide information recommending visit to the hospital.

Figure 13A:
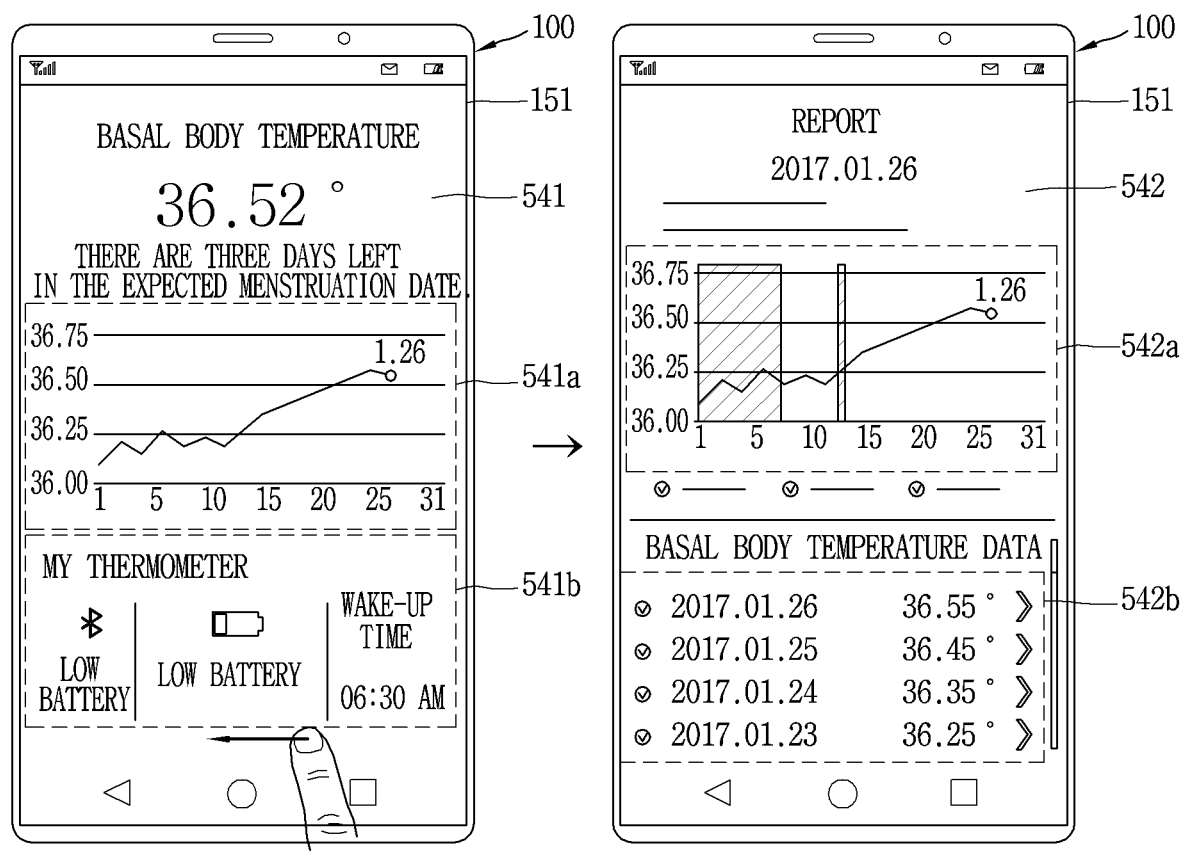
FIGS. 13A to 13C are conceptual diagrams illustrating a control method of an external device interworking with a thermometer according to the present invention.
Figure 13B:
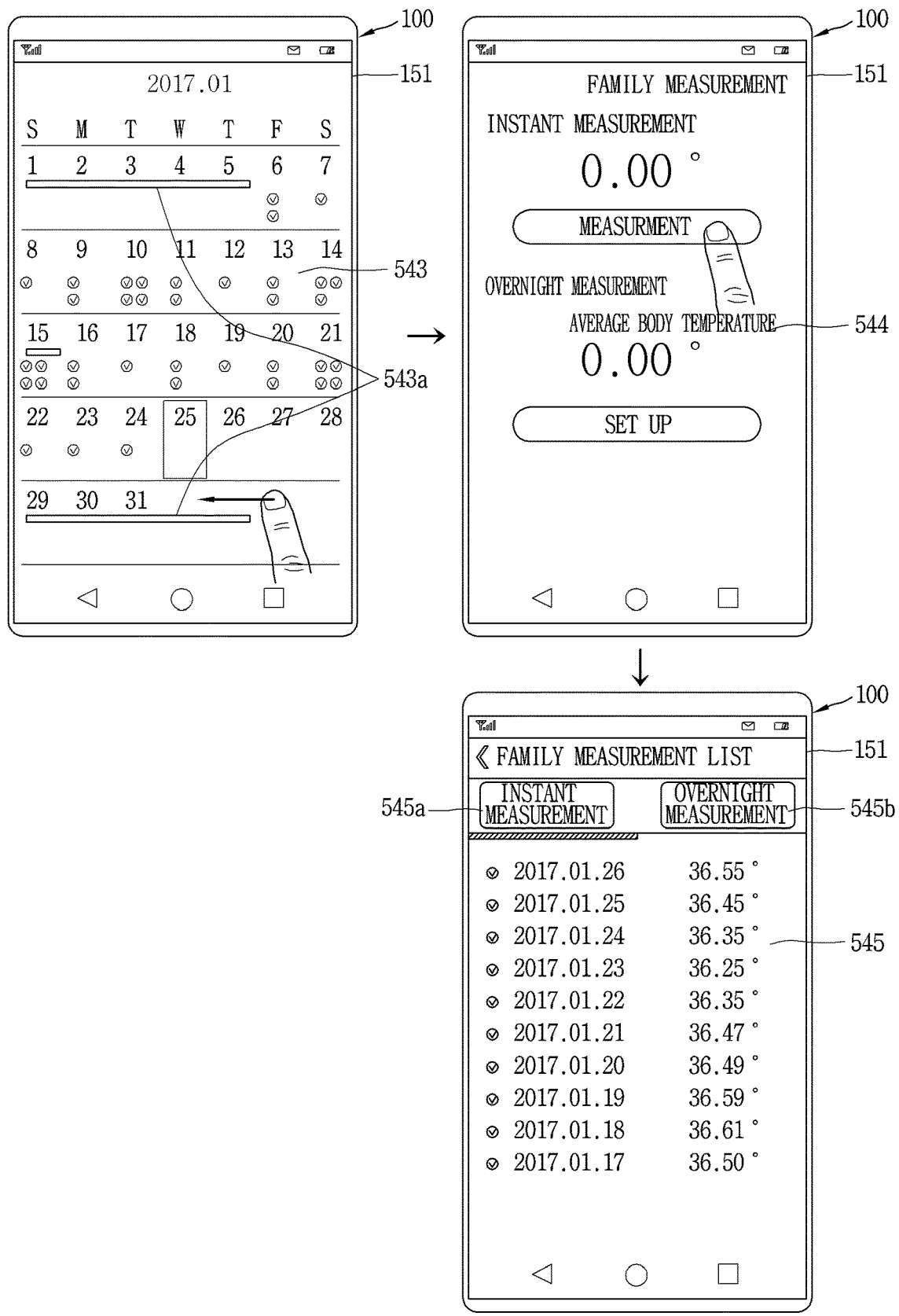
Figure 13C:
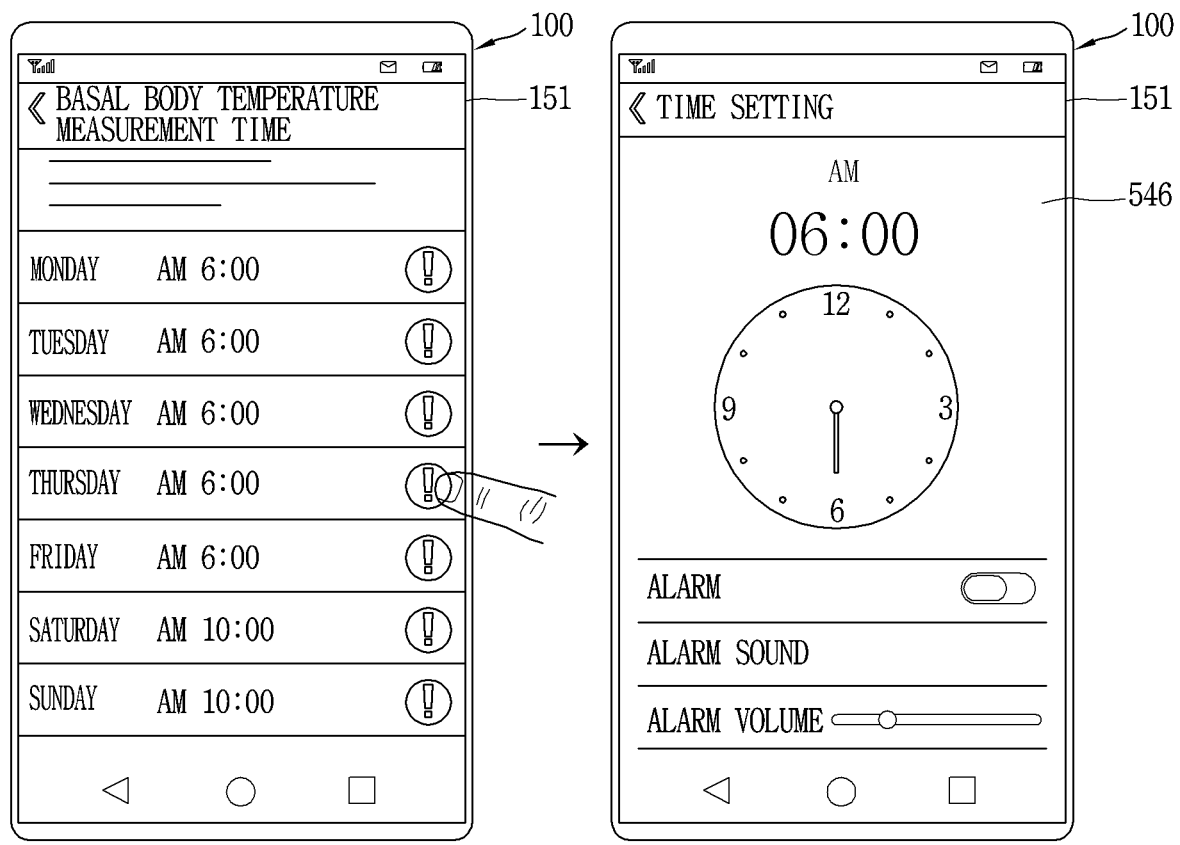

FIGS. 13A to 13C are schematic diagrams illustrating a control method of an external device cooperating with a thermometer according to the present invention.

Referring to FIG. 13A, the display unit 151 of the external device 100 outputs a first execution screen 541 when a specific application is executed. The first execution screen 541 may display the basal body temperature measured before waking up today as numerical value thereof and may include information on the temperature rise/fall compared with the basal body temperature yesterday. It may also include guide information on menstruation, pregnancy and ovulation. Here, the basal body temperature is set to the lowest body temperature measured 12 times at intervals of 10 minutes for 2 hours from 2 hours before the wake-up time.

The first execution screen 541 includes a graph 541*a* showing a variation amount of the basal body temperature by date and driving information 541*b* of the thermometer 1000.

When a specific touch input is applied to the first execution screen 541, a second execution screen 542 is output. The second execution screen 542 includes history information of the measured body temperature. The controller forms the menstrual cycle pattern data based on the measured body temperature information, and the second execution screen 542 includes a graph 542*a* according to the pattern data. The graph 542*a* represents a change in body temperature, and includes information about a menstruation date, an ovulation date and a pregnantable period.

In addition, the second execution screen 542 includes a basal body temperature data list 542*b* recorded for each date.

Referring to FIG. 13B, the display unit 151 outputs a third execution screen 543 which may be a calendar screen. The calendar screen 543 records the measured basal body temperature and includes data (whether or not menstruation, whether or not sexual intercourse, whether or not taking or injection of ovulation inducer, whether or not taking cold medicine or antibiotic, memo, etc.) stored by the user.

Accordingly, the user can grasp the data of the basal body temperature as well as the basal body temperature at a glance through the calendar screen.

The third execution screen 543 may be switched to the fourth execution screen 544 based on a specific touch input of the specific method applied on the third execution screen 543. The fourth execution screen 544 corresponds to a control screen for controlling the body temperature measurement.

According to the present embodiment, the body temperature of a person other than the set user can be measured and recorded. In this case, rather than the basal body temperature, the current body temperature can be measured in real time using the thermometer 1000. When a touch input is applied to the fourth execution screen 454, a body temperature measurement by the thermometer 1000 is performed according to a control signal.

Also, unlike the measurement of the basal body temperature about 2 hours before the waking-up, it is possible to measure the body temperature for a predetermined time and to be notified when the temperature exceeds a specific temperature range. Although not specifically shown in the Figure, the measured body temperature information can be transmitted to the external device 100 in real time. When the received body temperature information satisfies a specific condition, the external device 100 can output an alarm if the body temperature is out of a predetermined range of a predetermined body temperature.

The external device 100 may output the list of measured data to the fifth execution screen 545. The fifth execution screen 545 may optionally include data measured instantly by the user's choice or data measured overnight.

FIG. 13C shows a display unit 151 for outputting a screen for setting a body temperature measurement start time. The screen for setting may display the measurement time by days of the week, and when one day of the week is selected, a sixth execution screen 546 for changing the time is output.

Figure 14A:
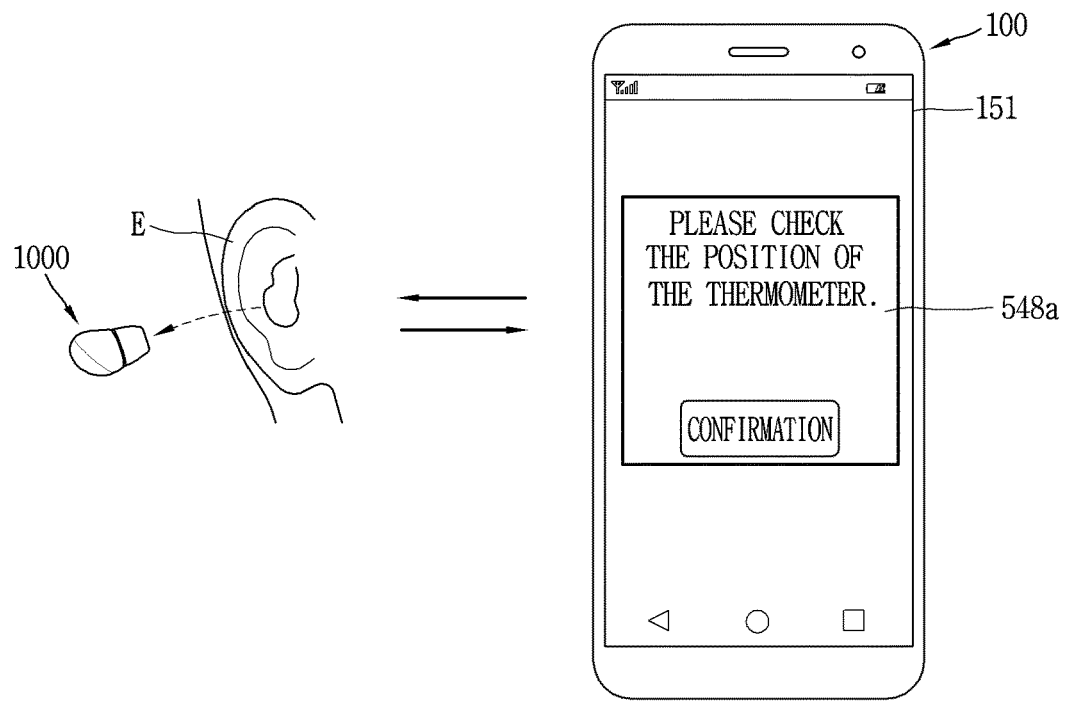
FIGS. 14A to 14C are conceptual diagrams illustrating a control method of an external device that outputs notification information indicating a driving state of the thermometer.
Figure 14B:
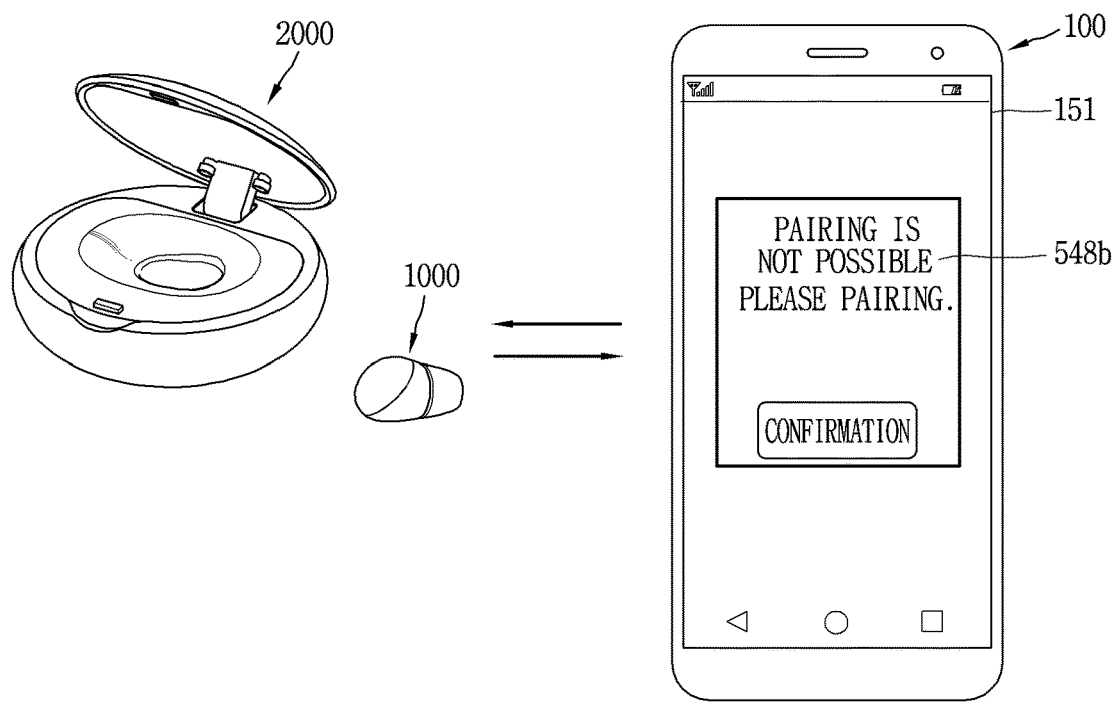
Figure 14C:
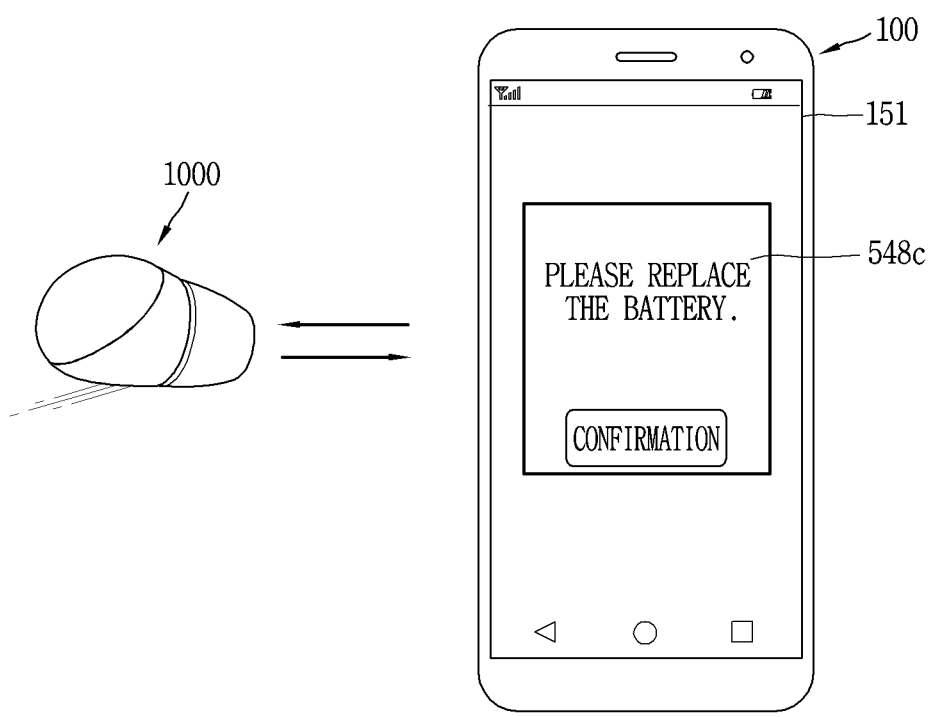

FIGS. 14A to 14C are schematic diagrams illustrating a control method of an external device that outputs notification information informing the driving state of the thermometer.

The thermometer 1000 according to the present embodiment may transmit the body temperature information and/or the driving state information sensed by the external device 100 in real time.

If the external device 100 does not receive the body temperature information within the normal range after the predetermined temperature measurement start time, the external device 100 detects the abnormal state of the measurement and outputs a first warning image 548A. The first warning image 548A may be the form of text or image that requests to confirm the position of the thermometer, and may output vibration or sound.

Referring to FIG. 14B, the thermometer 1000 transmits the body temperature information to the external device 100 when the thermometer 1000 is received in the receiving device 2000. The external device 100 outputs a second warning image 548B when the body temperature information is not received. The second warning image 548B may include information that the pairing is not possible.

In this case, a memory included in the thermometer 1000 may temporarily store information. Accordingly, when the pairing state corresponds to the normal range, all stored information can be transmitted to the external device.

Referring to FIG. 14C, the external device 100 may output a third warning image 548c indicating a shortage of the battery of the thermometer 1000. The external device 100 may output the third warning image 548c when the received body temperature information is irregular. Alternatively, the thermometer 1000 may transmit information on the battery shortage to the external device 100 as a radio signal.

The control method according to the embodiment can be activated and deactivated by the user's setting.

Figure 15A:
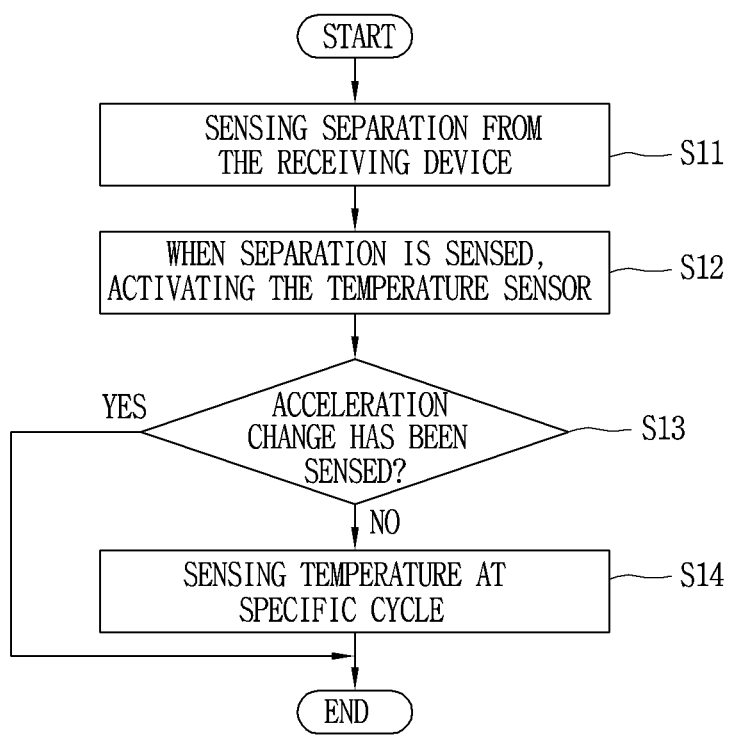
FIGS. 15A and 15B are schematic diagrams illustrating a control method of allowing a body temperature sensing to be performed according to detection of acceleration.
Figure 15B:
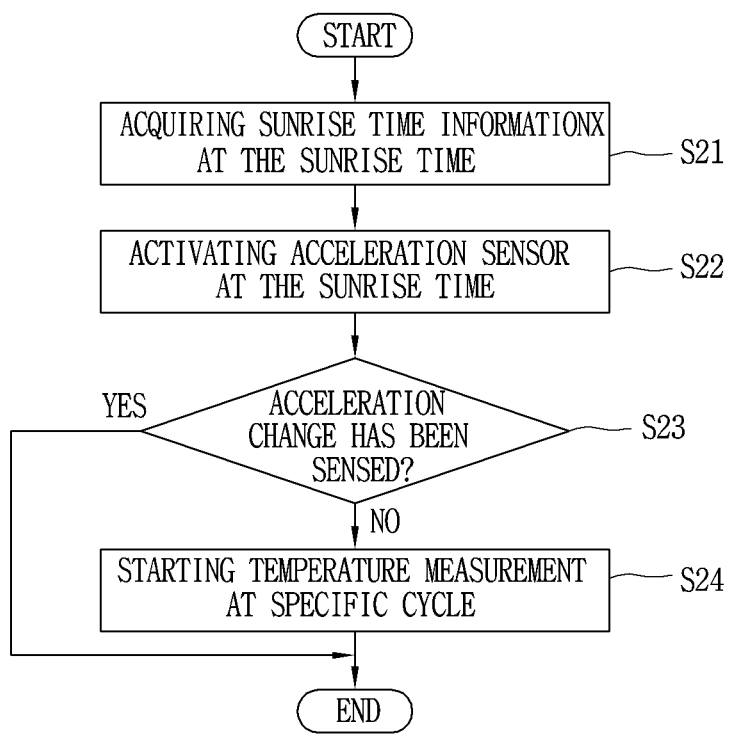

FIGS. 15A and 15B are schematic diagrams illustrating a control method of allowing a body temperature sensing to be performed according to detection of acceleration.

Referring to FIG. 15A, the thermometer 1000 activates a temperature sensor (S12) when a separation from the receiving device 2000 is sensed (S11). If no change in acceleration is detected by the sensing unit included in the wearable device (S13), the sensing unit senses the temperature in a specific period (S14).

That is, it is assumed that when there is no movement in which the acceleration change is not detected and when the measured temperature value corresponds to the body temperature range, it is a sleep state. According to the present embodiment, the temperature measurement may be started based on whether or not there is movement.

Referring to FIG. 15B, sunrise time information based on the location information of the user (the external device 100) is acquired (S21). The wearable device activates a sensing unit (acceleration sensor) based on the sunrise time information. For example, the sensing unit is activated two hours before the sunrise.

Whether or not there is a change in the acceleration is sensed (S23). If the acceleration is not changed, the temperature can be measured at a specific period (S24).

According to the present embodiment, the body temperature information can be collected by more accurately grasping the situation that may be considered as a sleep state.

Figure 16:
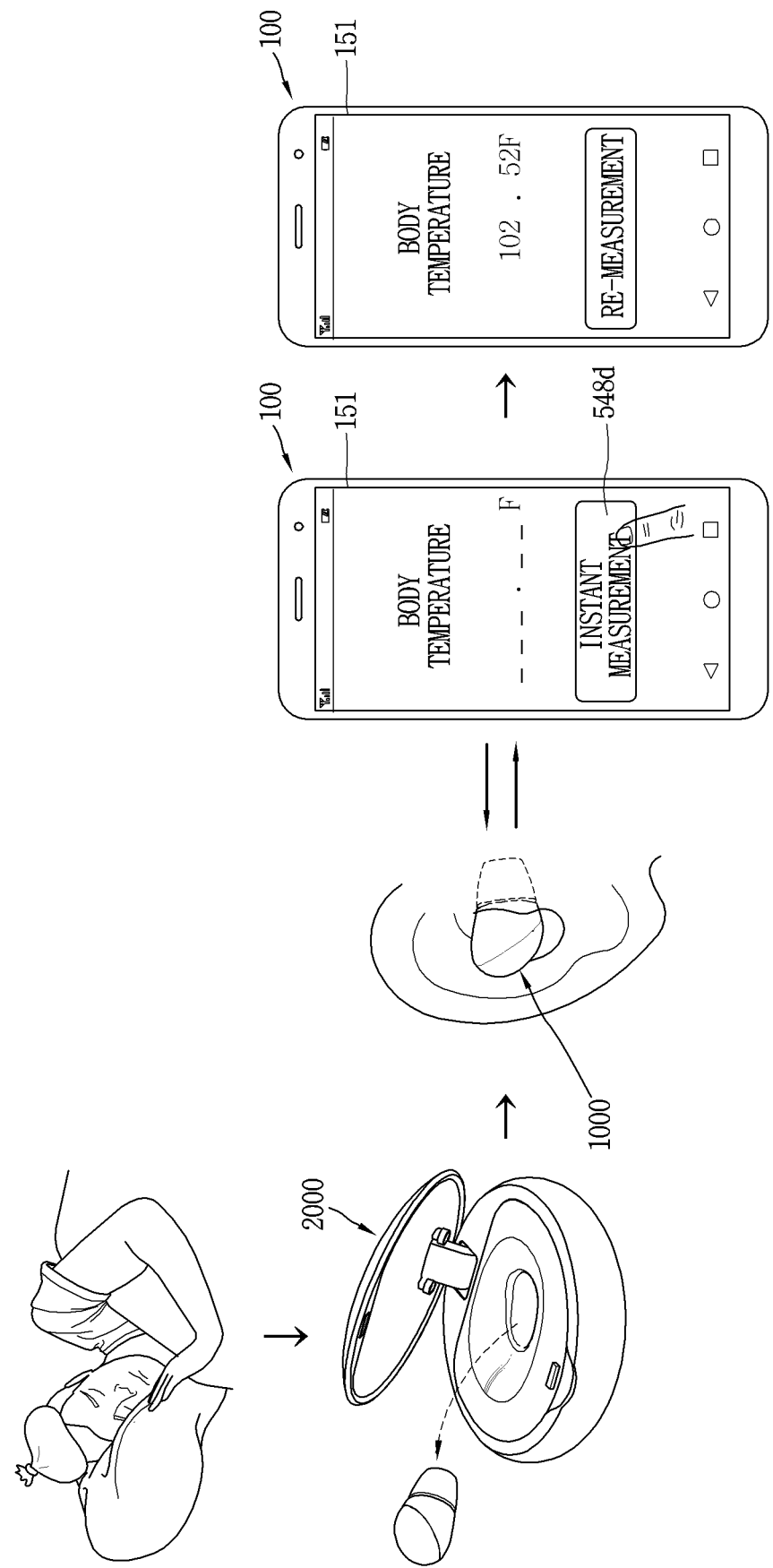
FIG. 16 is a conceptual diagram illustrating an instant measurement function.

FIG. 16 is a schematic diagram illustrating the measurement function.

Referring to FIG. 16, the thermometer 1000 can sense the body temperature in real time. When the thermometer 1000 is separated from the receiving unit 2000, the power of the thermometer 1000 is turned on.

The thermometer 1000 can be controlled to measure the body temperature in real time through the external device 100. The thermometer 1000 transmits the sensed body temperature information to the external device 100. Accordingly, the display unit 151 of the external device 100 can output the received body temperature information.

Figure 17:
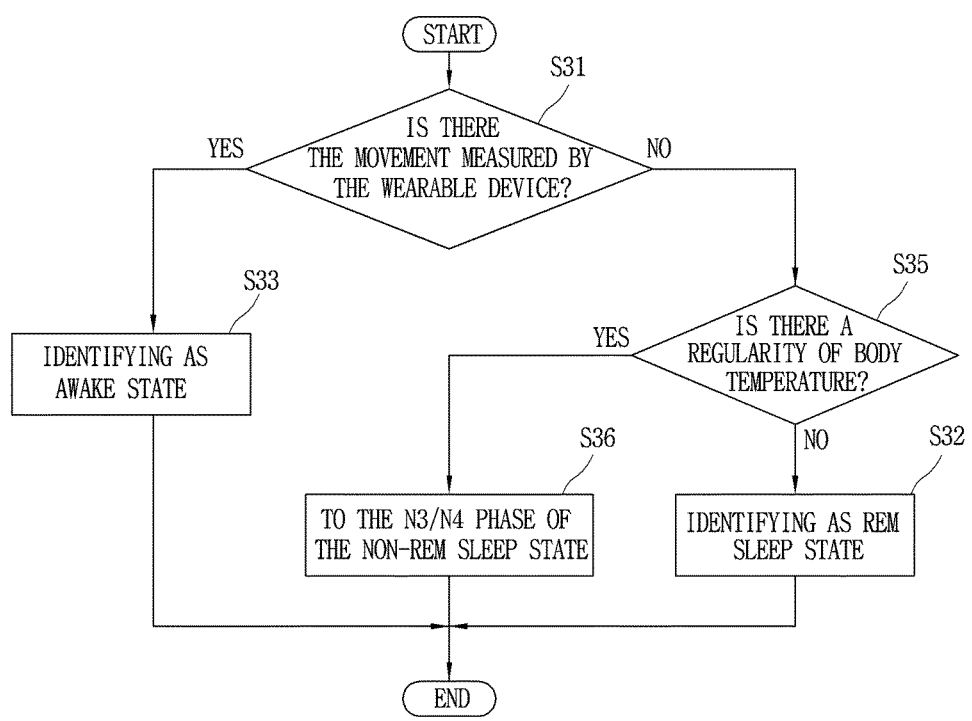
FIG. 17 is a view illustrating a control method for analyzing a sleep state in cooperation with a wearable device.

FIG. 17 illustrates a control method for analyzing the sleep state in cooperation with a wearable device.

The wearable device according to the present embodiment may be any one of a watch type terminal, a ring type terminal and a glass type terminal that can be worn on a wrist, a finger and a head. The wearable device includes a sensing unit that is worn in one region of the user's body and senses the movement of the user's body. The sensing unit may include an acceleration sensor, a gyro sensor, or the like. According to the present embodiment, the sleep state can be accurately analyzed through the body temperature information sensed through the thermometer and the movement information sensed by the wearable device.

Here, the sleep state can be distinguished as a deep sleep state, a light sleep state, and a wake state (awake). It is important to distinguish between the N3/N4 state and the REM sleep state, which have substantially the same degree of movement during the sleep phase, in determining the depth of the sleep. However, the use of the wearable device based on the acceleration sensor alone cannot distinguish between the REM sleep phase and the non-REM 3/4 phase because the sleep phase is determined only by the movement. In addition, although there is movement in the wake-up state, only the movement information of the sensing unit cannot identify the wake-up state. Therefore, more accurate sleep analysis can be performed by analyzing the movement information of the wearable device and the body temperature of the thermometer 1000 together.

Therefore, if the body temperature is irregular and movement is not detected, it is determined as REM sleep state. If the body temperature is stable while the movement is not detected, the state is identified as N3/N4 state. The REM sleep state is mainly a dream phase in which the cerebrum is highly active and there is no movement of the body, but the movement of the eye is active. The N1 state is a transient state between complete sleep and awake, and the N2 state is a state in which the amplitude and frequency of brainwaves decrease and slowly enters a deep sleep state. The N3/N4 state corresponds to the deep sleep state and thus to the deepest sleep phase.

Referring to FIG. 17, it is determined whether movement has been measured by the wearable device (S31). If movement is detected, it is determined whether the body temperature is regular or whether the body temperature is stable (S35). If the movement is detected and the body temperature is regular and stable, it is identified as the N3/N4 level in the non-REM sleep state (S36). If the body temperature is not regular and stable, it is identified as the REM sleep state.

When a movement is detected by the wearable device, it is identified as a wake-up state (awake) (S33). However, if the movement is determined as a minute movement (degree of backwardness) according to a specific criterion, it may be identified as the N1/N2 phase of the non-REM sleep.

Thus, it is possible to more accurately grasp the sleeping phase through body temperature sensing and movement detection.

The present invention described above can be implemented as computer readable codes on a medium on which a program is recorded. The computer readable medium encompasses all kinds of recording devices in which data that can be read by a computer system is stored. Examples of the computer-readable medium include a hard disk drive (HDD), a solid state disk (SSD), a silicon disk drive (SDD), a ROM, a RAM, a CD-ROM, a magnetic tape, a floppy disk and so on. The computer-readable medium may also be implemented in the form of a carrier wave (e.g., transmission over the Internet). In addition, the computer may include a controller 180 of the terminal. Accordingly, the above detailed description should be considered in all respects as illustrative and not restrictive. The scope of the present invention should be determined by rational interpretation of the appended claims, and all changes within the scope of equivalents of the present invention are included in the scope of the present invention.

What is claimed is:

1. A thermometer comprising:
    a main body extending in a first direction, the main body including:
        a first body having first and second regions; and
        a second body mounted on the first body;
    a rubber cap surrounding the second region of the first body and configured to be inserted into an ear of a user;
    a temperature sensor disposed in the second region of the first body and configured to sense a temperature, the temperature sensor having a specific temperature sensing range with respect to the first direction; and
    first and second circuit boards electrically connected to the temperature sensor, the first and second circuit boards being disposed in the second region of the first body in a second direction intersecting the first direction,
    wherein the first body and the rubber cap include first and second holes, respectively, to expose the temperature sensor,
    wherein the first body has one end extending parallel to the first and second circuit boards,
    wherein the second body is mounted on the one end of the first body,
    wherein the thermometer further comprising a flexible circuit board connecting the temperature sensor and the first circuit board,
    wherein the flexible circuit board includes a bent region, and
    wherein one end of the flexible circuit board is connected to a region of the temperature sensor closest to the first circuit board.

2. The thermometer of claim 1, wherein an inner surface of the second region of the first body defining the first hole is an oblique surface,
    wherein an inner surface of the rubber cap defining the second hole is an oblique surface,
    wherein the first and second oblique surfaces are arranged such that the first and second holes increase in size in a direction moving away from the temperature sensor, and
    wherein the first and second oblique surfaces are at a specific angle to include the specific temperature sensing range of the temperature sensor.

3. The thermometer of claim 1, wherein the second region of the first body includes a fixing groove formed along an inner circumferential surface thereof, and
    wherein the rubber cap includes a fixing protrusion corresponding to the fixing groove on an inner surface thereof so as to fix the rubber cap to the second region of the first body.

4. The thermometer of claim 3, further comprising a vent hole extending from a boundary of the first and second regions of the first body to an end of the second region of the first body spaced from the boundary of the first and second regions of the first body, the vent hole being provided as a recess from an outer surface of the second region of the first body,
    wherein a gap is provided between the first and second regions of the first body and the rubber cap to allow air to flow into the vent hole.

5. The thermometer of claim 4, wherein the fixing groove intersects the vent hole, and
    wherein one region of the vent hole intersected by the fixing groove is deeper than a depth of the fixing groove.

6. The thermometer of claim 1, wherein the second body extends along the first direction from another end of the first body opposite the one end of the first body, and
    wherein an outer circumference of the second body is smaller than an outer circumference of the first body.

7. The thermometer of claim 1, further comprising:
    a first module, a second module and a third module mounted on the first body,
    wherein the first module is coupled to the first body and disposed at the one end of the first body in the first direction, and
    wherein the first and second circuit boards are disposed on one surface of the first module,
    wherein the second module is coupled to the first module and formed to surround a peripheral region of the first and second circuit boards, and
    wherein the third module is coupled to the second module and supports the temperature sensor in the first direction.

8. The thermometer of claim 7, further comprising:
    a battery; and
    a side wall portion provided on another surface of the first module so as to surround the battery, the side wall portion having a thread, wherein the second body includes an inner surface provided so as to surround the side wall portion, the inner surface having a thread, and wherein the first and second bodies are configured to be separated by rotation relative to each other.

9. The thermometer of claim 7, wherein the first body includes first and second grooves that intersect each other, and wherein the second body includes a coupling protrusion configured to move along the first groove and into the second groove to be fixed to the second groove.

10. The thermometer of claim 7, wherein the second module includes a side wall portion that surrounds the first and second circuit boards, and a supporting portion protruding from the side wall portion between the first and second circuit boards to support the first and second circuit boards.

11. The thermometer of claim 10, wherein an outer surface of the side wall portion corresponds to a region of an outer surface of the first region of the first body.

12. The thermometer of claim 10, wherein the third module includes a sensor supporting portion to support the temperature sensor and first and second fixed hook portions extending from the sensor supporting portion, the sensor supporting portion being mounted on the second module via the hook portions, and wherein the first and second fixed hook portions have different lengths.

13. The thermometer of claim 12, wherein each end of the first and second fixed hook portions includes a hook structure projecting in a direction away from each other, wherein an inner surface of the side wall portion of the second module includes first and second fixing recesses corresponding to the first and second fixed hook portions, respectively, to allow the hook structures of the first and second fixed hook portions to be inserted thereinto, and wherein each of the first and second fixing recesses is formed adjacent to the first circuit board.

14. The thermometer of claim 7, further comprising an antenna disposed on one side of the first module, the antenna being configured to wirelessly transmit measured body temperature information to an external device.

* * * * *